United States Patent
Ghanekar et al.

(10) Patent No.: US 10,684,275 B2
(45) Date of Patent: Jun. 16, 2020

(54) METHODS AND COMPOSITIONS FOR OBTAINING A TUBERCULOSIS ASSESSMENT IN A SUBJECT

(71) Applicant: Becton, Dickinson and Company, Franklin Lakes, NJ (US)

(72) Inventors: Smita Ghanekar, Fremont, CA (US); Marja Suni, Los Gatos, CA (US); Margaret Inokuma, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 108 days.

(21) Appl. No.: 15/824,964

(22) Filed: Nov. 28, 2017

(65) Prior Publication Data
US 2018/0164287 A1    Jun. 14, 2018

Related U.S. Application Data

(60) Provisional application No. 62/434,328, filed on Dec. 14, 2016.

(51) Int. Cl.
*G01N 33/50* (2006.01)
*C12N 5/0783* (2010.01)
(Continued)

(52) U.S. Cl.
CPC ......... *G01N 33/505* (2013.01); *C12N 5/0638* (2013.01); *G01N 33/5695* (2013.01); (Continued)

(58) Field of Classification Search
CPC ............ G01N 33/505; G01N 33/5023; G01N 33/5047; G01N 33/5695; G01N 33/56972;
(Continued)

(56) References Cited

U.S. PATENT DOCUMENTS 5,955,077 A    9/1999  Andersen et al.
7,115,361 B2  10/2006  Lalvani et al.
(Continued)

FOREIGN PATENT DOCUMENTS

CN    102062774 A    5/2011
EP      1152012 B1    7/2007
(Continued)

OTHER PUBLICATIONS

Caccamo et al. Phenotypical and Functional Analysis of Memory and Effector Human CD8 T Cells Specific for Mycobacterial Antigens. The Journal of Immunology 177: 1780-1785 (2006).*

(Continued)

*Primary Examiner* — Gailene Gabel
(74) *Attorney, Agent, or Firm* — Kathleen Y. Rao; Bret E. Field; Bozicevic, Field & Francis LLP

(57) ABSTRACT

Methods for obtaining a tuberculosis assessment in a subject are provided. Aspects of the methods include assaying a tuberculosis (TB) activated sample from the subject for at least one of: (i) CD154$^+$ T cells; and (ii) T cells having a central memory phenotype, such as a CM1 phenotype, CM2 phenotype or a CM3 phenotype; to obtain a TB biomarker signature, and then deriving a tuberculosis assessment for the subject from the TB biomarker signature. Aspects of the invention further include reagents, devices, systems, and kits thereof that find use in practicing the subject methods are provided. The methods and compositions find use in a variety of applications, including TB diagnosis and monitoring of TB treatment.

15 Claims, 1 Drawing Sheet

TB antigen-specific CD154-positive T cells

(51) Int. Cl.
  *G01N 33/68* (2006.01)
  *G01N 33/569* (2006.01)
  *G01N 15/10* (2006.01)
  *G01N 15/14* (2006.01)

(52) U.S. Cl.
  CPC ... *G01N 33/56972* (2013.01); *G01N 33/6869* (2013.01); *G01N 15/1459* (2013.01); *G01N 2015/1006* (2013.01); *G01N 2333/7051* (2013.01); *G01N 2333/70514* (2013.01); *G01N 2333/70517* (2013.01); *G01N 2333/70521* (2013.01); *G01N 2333/70575* (2013.01); *G01N 2333/70578* (2013.01); *G01N 2333/70589* (2013.01)

(58) Field of Classification Search
  CPC ........... G01N 33/6869; G01N 33/4915; G01N 15/1459; G01N 2015/1006; G01N 2333/70514; G01N 2333/70517; G01N 2333/70521; G01N 2333/7051; G01N 2333/70575; G01N 2333/70578; G01N 2333/70589; C12N 5/0636; C12N 5/0638
  See application file for complete search history.

(56) References Cited

U.S. PATENT DOCUMENTS

| | | |
|---|---|---|
| 7,135,280 B2 | 11/2006 | Lalvani |
| 7,579,141 B2 | 8/2009 | Gennaro |
| 7,709,211 B2 | 5/2010 | Gennaro |
| 8,021,832 B2 | 9/2011 | Gennaro |
| 8,053,181 B2 | 11/2011 | Lewinsohn et al. |
| 8,105,797 B2 | 1/2012 | Lalvani |
| 8,216,795 B2 | 7/2012 | Lalvani et al. |
| 8,361,707 B2 | 1/2013 | Lewinsohn et al. |
| 8,507,211 B2 | 8/2013 | Lalvani et al. |
| 8,617,821 B2 | 12/2013 | Lalvani et al. |
| 8,623,609 B2 | 1/2014 | Gennaro et al. |
| 8,658,350 B2 | 2/2014 | Lewinsohn et al. |
| 8,697,091 B2 | 4/2014 | Vordermeier et al. |
| 8,765,366 B2 | 7/2014 | Lalvani et al. |
| 9,005,902 B2 | 4/2015 | Lalvani et al. |
| 9,040,233 B2 | 5/2015 | Lewinsohn et al. |
| 9,110,061 B2 | 8/2015 | Mariani et al. |
| 9,146,236 B2 | 9/2015 | Pantaleo et al. |
| 9,173,930 B2 | 11/2015 | Lewinsohn et al. |
| 9,238,066 B2 | 1/2016 | Gennaro |
| 9,340,622 B2 | 5/2016 | Agrewala et al. |
| 9,360,480 B2 | 6/2016 | Lalvani et al. |
| 9,377,460 B2 | 6/2016 | Lalvani |
| 9,476,877 B2 | 10/2016 | Bahlmann et al. |
| 9,526,773 B2 | 12/2016 | Aagaard et al. |
| 2001/0006789 A1 | 7/2001 | Maino et al. |
| 2003/0027774 A1 | 2/2003 | Hendrickson et al. |
| 2004/0141985 A1 | 7/2004 | Lalvani et al. |
| 2007/0196878 A1 | 8/2007 | Goletti et al. |
| 2007/0224122 A1 | 9/2007 | Gennaro |
| 2007/0224123 A1 | 9/2007 | Gennaro |
| 2008/0305503 A1 | 12/2008 | Lalvani |
| 2009/0170120 A1 | 7/2009 | Lalvani et al. |
| 2010/0016415 A1 | 1/2010 | Gennaro |
| 2010/0129391 A1 | 5/2010 | Reed et al. |
| 2010/0203568 A1 | 8/2010 | Lalvani et al. |
| 2010/0317036 A1 | 12/2010 | Vordermeier et al. |
| 2011/0070599 A1* | 3/2011 | Park ................... G01N 33/5695 435/7.24 |
| 2011/0183342 A1 | 7/2011 | Lewinsohn et al. |
| 2011/0201044 A1 | 8/2011 | Lalvani et al. |
| 2012/0014881 A1 | 1/2012 | Lewinsohn et al. |
| 2012/0128708 A1 | 5/2012 | Lalvan |
| 2012/0264141 A1 | 10/2012 | Lalvani et al. |
| 2012/0282181 A1 | 11/2012 | Lewinsohn et al. |
| 2013/0101523 A1 | 4/2013 | Lewinsohn et al. |
| 2013/0122523 A1 | 5/2013 | Bahlmann et al. |
| 2013/0149719 A1 | 6/2013 | Gennaro |
| 2013/0209500 A1 | 8/2013 | Reed et al. |
| 2013/0252260 A1 | 9/2013 | Mariani et al. |
| 2013/0310271 A1 | 11/2013 | Lalvani et al. |
| 2013/0338059 A1 | 12/2013 | Pantaleo et al. |
| 2014/0087399 A1 | 3/2014 | Lalvani et al. |
| 2014/0220600 A1 | 8/2014 | Gennaro |
| 2014/0377300 A1 | 12/2014 | Anantha et al. |
| 2015/0010927 A1 | 1/2015 | Escalante |
| 2015/0204885 A1 | 7/2015 | Poulakis et al. |
| 2015/0219645 A1 | 8/2015 | Lewinsohn et al. |
| 2015/0253324 A1 | 9/2015 | Moritz et al. |
| 2015/0290311 A1 | 10/2015 | Aagaard et al. |
| 2015/0309023 A1 | 10/2015 | Mariani et al. |
| 2016/0069920 A1 | 3/2016 | Holmes et al. |
| 2016/0070884 A1 | 3/2016 | Lui et al. |
| 2016/0103127 A1 | 4/2016 | Lewinsohn et al. |
| 2016/0195529 A1 | 7/2016 | Lalvani et al. |
| 2017/0008938 A1 | 1/2017 | Rehm et al. |

FOREIGN PATENT DOCUMENTS

| | | | |
|---|---|---|---|
| EP | 1214088 B1 | 4/2009 | |
| EP | 1561106 B1 | 4/2009 | |
| EP | 1144447 B1 | 10/2009 | |
| EP | 1723426 B1 | 4/2010 | |
| EP | 1520174 B1 | 2/2011 | |
| EP | 2309260 A1 | 4/2011 | |
| EP | 1390755 B1 | 10/2012 | |
| EP | 2005182 B1 | 5/2013 | |
| EP | 1735623 B1 | 9/2013 | |
| EP | 2207035 B1 | 10/2013 | |
| EP | 2397856 B1 | 11/2013 | |
| EP | 2397852 B1 | 12/2013 | |
| EP | 2397853 B1 | 1/2014 | |
| EP | 2428801 B1 | 5/2014 | |
| EP | 2397854 B1 | 6/2014 | |
| EP | 2385371 B1 | 10/2014 | |
| EP | 2417456 B1 | 7/2016 | |
| WO | WO2001079274 A2 | 10/2001 | |
| WO | WO2005080990 A2 | 9/2005 | |
| WO | WO2005090988 A2 | 9/2005 | |
| WO | WO2010070581 A1 | 6/2010 | |
| WO | WO2010115989 A1 | 10/2010 | |
| WO | WO 2011/113953 * | 9/2011 | ........... G01N 33/569 |
| WO | WO2011113953 A1 | 9/2011 | |
| WO | WO2012085652 A2 | 6/2012 | |
| WO | WO2014023984 A2 | 2/2014 | |
| WO | WO2014063704 A2 | 5/2014 | |
| WO | WO2014140833 A2 | 9/2014 | |
| WO | WO2015033136 A1 | 3/2015 | |
| WO | WO2015035260 A1 | 3/2015 | |
| WO | WO2015114351 A1 | 8/2015 | |
| WO | WO2015119512 A1 | 8/2015 | |
| WO | WO2015134928 A2 | 9/2015 | |

OTHER PUBLICATIONS

Steitz et al. Discrimination of active pulmonary TB against a background of high TB exposure and latent infection. American Journal of Respiratory and Critical Care Medicine. Submitted Draft: 1-28 (2010).*

Adekambi, et al. "Biomarkers on patient T cells diagnose active tuberculosis and monitor treatment response", jci.org, vol. 125, No. 5 May 2015, pp. 1827-1838.

BD Biosciences, "Cytokine Detection in Antigen-Activated CD8+ and CD4+ T Cells", 2002, www.bdbiosciences.com, 16 pages.

Caccamo, et al. "Phenotypical and Functional Analysis of Memory and Effector Human CD8 T Cells Specific for Mycobacterial Antigens", J Immunol Aug. 1, 2006, 177 (3) 1780-1785.

Pollock, et al "T-Cell Immunophenotyping Distinguishes Active From Latent Tuberculosis", JID 2013:208, 2013, pp. 952-968.

* cited by examiner

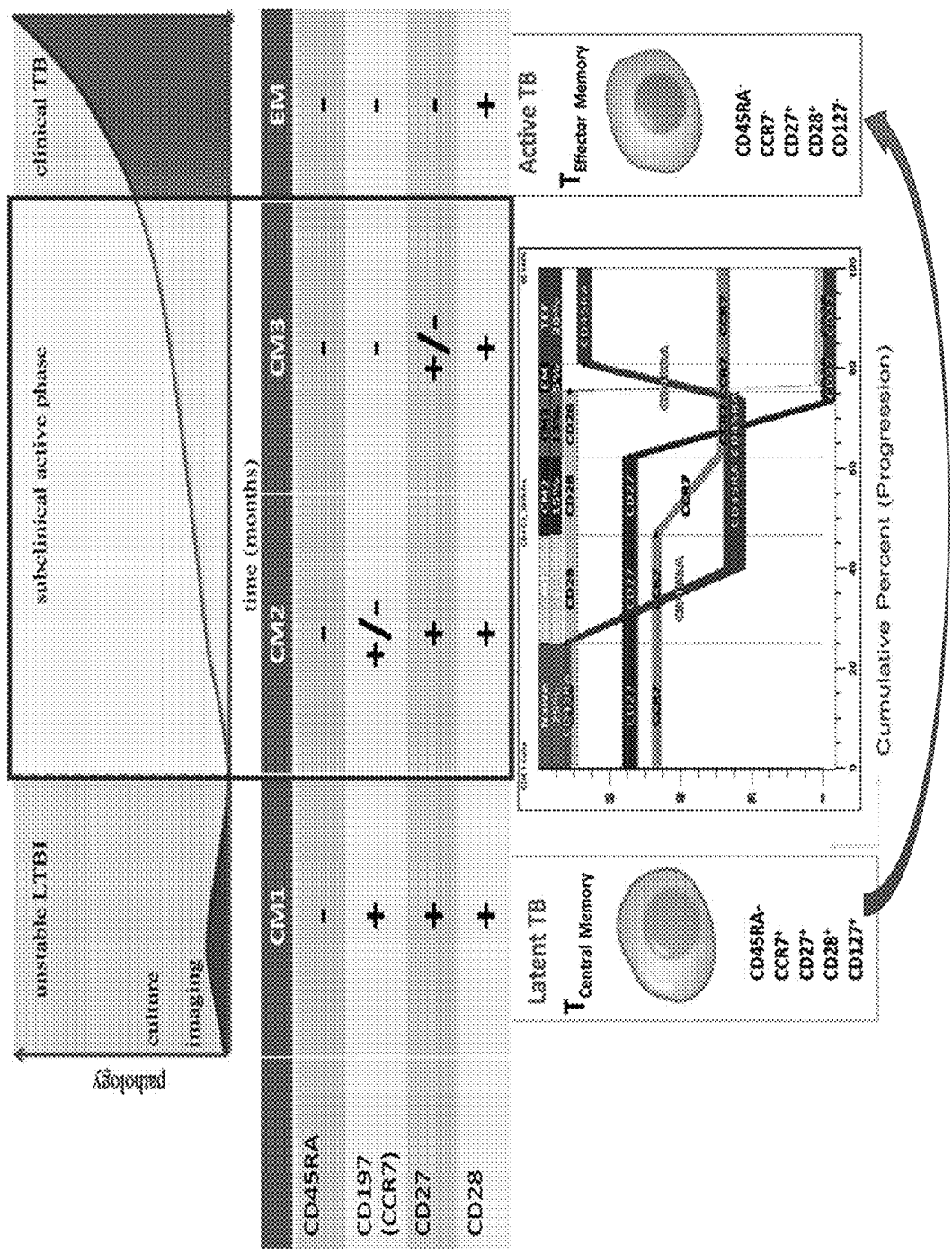

METHODS AND COMPOSITIONS FOR OBTAINING A TUBERCULOSIS ASSESSMENT IN A SUBJECT

CROSS-REFERENCE TO RELATED APPLICATION

Pursuant to 35 U.S.C. § 119(e), this application claims priority to the filing date of U.S. Provisional Patent Application Ser. No. 62/434,328, filed Dec. 14, 2016; the disclosure of which application is incorporated herein by reference.

INTRODUCTION

TB disease is caused by a bacterium called *Mycobacterium tuberculosis* (Mtb). The bacteria commonly infect the lungs, but TB bacteria can also infect any other part of the body, including, e.g., the kidney, the spine, and the brain. If not treated properly, TB disease can be fatal. TB is generally transmitted through the air from an infected person to a second person, e.g., when a person with a TB infection or TB disease of the lungs or throat coughs, sneezes, speaks, or sings and airborne bacteria are inhaled by a second person.

About one-third of the world's population has latent TB, which means people have been infected by TB bacteria but are asymptomatic and cannot transmit the disease. According to the World Health Organization (WHO), TB is second only to HIV/AIDS as the greatest killer worldwide due to a single infectious agent. For example, in 2012, 8.6 million people fell ill with TB and 1.3 million died from TB. Furthermore, TB is highly prevalent in the developing world with over 95% of TB deaths occurring in low- and middle-income countries. TB is among the top three causes of death for women aged 15 to 44. TB is also highly prevalent in children. For example, in 2012, an estimated 530,000 children became ill with TB and 74,000 HIV-negative children died of TB. Co-infection of TB and HIV remains a significant health burden as TB is a leading killer of people living with HIV causing one fifth of all deaths. Multi-drug resistant TB is present in virtually all countries surveyed by the WHO.

An individual infected may be asymptomatic. Someone with an active tuberculosis infection typically shows symptoms of a chronic cough and blood-tinged sputum referred to as a pulmonary active tuberculosis (ATB) infection. The asymptomatic or latent tuberculosis infections (LTBI) often do not progress to ATB for an individual with a healthy immune system. However, those with a compromised immune system, such as the elderly and those with HIV, have a much higher chance of developing life-threatening ATB.

SUMMARY

Methods for obtaining a tuberculosis assessment in a subject are provided. Aspects of the methods include assaying a tuberculosis (TB) activated sample from the subject for at least one of: (i) $CD154^+$ T cells; and (ii) T cells having a central memory phenotype, such as a CM1 phenotype, CM2 phenotype or a CM3 phenotype; to obtain a TB biomarker signature, and then deriving a tuberculosis assessment for the subject from the TB biomarker signature. Aspects of the invention further include reagents, devices, systems, and kits thereof that find use in practicing the subject methods are provided. The methods and compositions find use in a variety of applications, including TB diagnosis and monitoring of TB treatment.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following FIGURES.

FIG. 1 graphically illustrates TB-specific T cell differentiation markers to predict progression from Latent TB to Clinical (active) TB infection.

DETAILED DESCRIPTION

Methods for obtaining a tuberculosis assessment in a subject are provided. Aspects of the methods include assaying a tuberculosis (TB) activated sample from the subject for at least one of: (i) $CD154^+$ T cells; and (ii) T cells having a central memory phenotype, such as a CM1 phenotype, CM2 phenotype or a CM3 phenotype; to obtain a TB biomarker signature, and then deriving a tuberculosis assessment for the subject from the TB biomarker signature. Aspects of the invention further include reagents, devices, systems, and kits thereof that find use in practicing the subject methods are provided. The methods and compositions find use in a variety of applications, including TB diagnosis and monitoring of TB treatment.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

The present disclosure provides methods for making a TB assessment for a subject. By making a "TB assessment" or a "TB assessment of a subject", it is meant an evaluation of a subject with respect to TB, which evaluation may be in a variety of formats, including but not limited to: diagnosing the presence of TB in the subject, clinically monitoring TB in a subject, etc. Diagnosing TB includes, e.g., diagnosing TB disease and, in some instances, discriminating, e.g., between latent TB infection (LTBI), progressive TB disease, active TB (ATB), drug resistant TB disease, etc. An assessment that includes a TB diagnosis may also include a determination of a treatment or a course of treatment for a patient suspected of having a TB infection or TB disease. Clinically monitoring TB includes, e.g., evaluating the clinical progression of TB in a subject, including, e.g., evaluating the progression of TB in the subject, such as transitioning from LTBI to ATB, evaluating treatment effectiveness and patient response to treatment, evaluating treatment endpoints, post-treatment follow-up, etc.

TB assessments may be obtained through the production and analysis of a TB biomarker signature. In some instances a TB assessment, e.g., a TB diagnosis, is obtained through the detection of a particular TB biomarker signature obtained for a subject, e.g., a subject suspected of having TB. In other instances, a TB assessment, e.g., a clinical assessment, including but not limited to, e.g., a clinical assessment of TB disease state, a clinical assessment of TB disease progression, a clinical assessment of TB treatment progression or a clinical assessment of TB treatment outcome, is obtained through the detection of a TB particular biomarker signature obtained for a subject known to have TB.

TB Biomarker Signatures

TB assessments, as described herein, are made, either alone or in combination with other evaluations or factors (e.g., as described below), based on a TB biomarker signature. By "biomarker signature" is meant the presence, absence, or relative level, e.g., expression level, of one or more individual biomarkers as described herein. The number of biomarkers that make up a biomarker signature will vary and in some instances may range from 1 to 200, including, e.g., 1, 2, 3, 4, 5, 6, 7, 8, 9, 10, 11, 12, 13, 14, 15, 16, 17, 18, 19, 20, from 1 to 3, from 2 to 5, from 1 to 5, from 5 to 10, from 2 to 8, from 1 to 10, from 5 to 15, from 10 to 20, from 20 to 40, from 30 to 50, from 40 to 60, from 50 to 70, from 60 to 80, from 70 to 90, from 80 to 100, from 50 to 150, from 100 to 200, from 150 to 200, etc. In certain instances, a biomarker signature includes a qualitative evaluation of the biomarker, including, e.g., qualitative evaluation of the level or expression or change in level or expression of the biomarker. In some instances, a biomarker signature includes one or more quantitative measurements of a biomarker including e.g., measurements of the level of a biomarker or the expression level of a biomarker, including e.g., measurements of the absolute expression level of the biomarker, measurements of the relative expression level of the biomarker (e.g., relative to a second biomarker or a reference biomarker or reference biomarker level, etc.), measurements of the change in expression of a biomarker (e.g., the change in expression of a biomarker in response to a stimulus or the change in expression of a biomarker over time, etc.) and the like.

In some instances, a biomarker signature may include categorical measurements of one or more biomarkers. Categorical measurements of biomarkers of a biomarker signature may be qualitative or quantitative. In some instances, qualitative categorical measurements of biomarkers included in a biomarker signature are based on qualitative evaluations of biomarkers that are binned into categories based on binning criteria (e.g., present or absent; positive or negative; high or low; high, medium, or low; normal or abnormal; sufficient or deficient; detectable or undetectable; significant or not significant; not significant, significant, or very significant; etc.). In some instances, quantitative categorical measurements of biomarkers included in a biomarker signature are based on quantitative measurements of biomarkers that are binned into categories based on binning criteria (e.g., present or absent; positive or negative; high or low; high, medium, or low; normal or abnormal; sufficient or deficient; detectable or undetectable; significant or not significant; not significant, significant, or very significant; etc.). Binning criteria for categorizing biomarkers of a biomarker signature may vary and may be determined by any convenient means, including e.g., visual assessment of biomarker data, statistical assessment of biomarker data, empirical testing of biomarkers, hypothesis based testing of biomarkers or biomarker data, computer modeling of biomarker data, etc. In some instances, described in more detail elsewhere herein, binning is also referred to as thresholding and is used to categorize a biomarker as present or absent, high or low, or above or below a threshold.

In some embodiments, a biomarker signature includes a single evaluation or measurement of a biomarker for a particular sample, e.g., including a measurement of the amount of the biomarker present in the sample. For example, a biomarker signature may include a measurement of the amount of a particular protein biomarker present in a fluid sample, e.g., a blood sample of a subject. In some embodiments, a biomarker signature includes a plurality of evaluations or measurements of a biomarker for a particular sample, e.g., including a plurality of measurements of the level of a biomarker within a particular aspect of the sample. For example, a biomarker signature may include a plurality of measurements of the level of a biomarker present in or on the surface of a plurality of cells of a cellular sample, e.g., a blood sample.

In some instances, a biomarker signature may include a secondary measurement based on a plurality of primary measurements. Primary measurements may vary and include any and all individual biomarker measurements described herein. In some instances, primary measurements may include individual evaluations or measurements of biomarkers including, e.g., measurements of biomarkers within some aspect of a sample, including, e.g., measurements of the level of biomarkers of cells of a cellular sample. Secondary measurements may vary and will depend on the primary measurement or the plurality of primary measurements and in some instances include but are not limited to measurements of subgroups, subcategories, subpopulations and the like. In some instances, where a plurality of primary measurements represents the levels of a biomarker present in or on some aspect of a sample, a secondary measurement may include a quantification or categorization of the plurality of primary measurements. For example, where a plurality of primary measurements represents individual measurements of the levels of a particular biomarker for individual cells, a secondary measurement may represent further quantification of the biomarker levels of individual cells or, e.g., a categorization of the cells based on their individual biomarker level. TB biomarker signatures, although not limited to primary and secondary measurements or combinations thereof, may include essentially only primary measurements, essentially only secondary measurements, or any combination of primary and secondary measurements.

In certain embodiments, a TB biomarker signature that includes measurements of more than one biomarker allows for an assessment or determination of higher confidence than the assessment or determination that could be made by analysis of the biomarkers independently. In some instances, a TB biomarker signature that includes measurements of more than one biomarker allows for an assessment or determination that could not be made by analysis of any of the individual biomarkers or any sub-combination of the biomarkers of the biomarker signature. Such TB biomarker signatures may in some instances be referred to or derived from multidimensional analysis. In some instances, multidimensional analysis is performed using a combination of biomarkers that have or have not been shown to be statistically significant in differentiating two or more different groups, e.g., treatment groups or patient groups. For example, in some instances a first biomarker may be used in combination with a second biomarker wherein the first biomarker has not been shown to statistically differentiate two different groups independently and the second biomarker has been shown to statistically differentiate two different treatment groups or patient groups independently, or vice versa. In some instances where two biomarkers are used in combination that do not independently statistically differentiate two different groups the combination of markers can statistically differentiate two different groups. In other instances where two biomarkers are used in combination that do independently differentiate, e.g., statistically differentiate, different groups the combination of markers can more significantly differentiate the different groups.

In certain instances, a TB biomarker signature may include one or more identified or evaluated or measured subgroups or subpopulations or proportions of a population of a particular sample having a shared characteristic or shared particular aspect that may vary within the sample. By "subgroup" or "subpopulation" or "proportion", used interchangeably herein, is meant a portion of a larger group or a larger population of a sample that is differentiated from the larger group or larger population by one or more common characteristics or common aspects. For example, a subpopulation may share a common biomarker or characteristic or categorical biomarker level, including e.g., biomarker expression level. In some instances, a common characteristic or common aspect of a subgroup or subpopulation may be related to a shared biomarker, including but not limited to, e.g., shared presence or absence of a particular biomarker, shared level of a particular biomarker, shared expression of a particular biomarker, shared change in level of a particular biomarker, shared change in expression of a particular biomarker, etc. In some embodiments, a common characteristic or common aspect of a subgroup or subpopulation may be unrelated to a biomarker and may be some other aspect of the individual units of the subgroup or subpopulation. Other aspects, i.e. non-TB-biomarker aspects, of the individual units of the subgroup of subpopulation may vary and may be any convenient aspect of the individual units that may be determined, visualized, detected, measured, categorized, etc.

In certain instances, a population of which one or more subpopulations is a portion may be a population of cells, e.g., cells of a cellular sample or a portion of the cells of a cellular sample. Subpopulations of cells within a population may or may not be mutually exclusive, i.e., such subpopulations may or may not overlap and in some instances may overlap from 1% to 100%, including e.g., from 1% to 10%, from 10% to 20%, from 20% to 30%, from 30% to 40%, from 40% to 50%, from 50% to 60%, from 60% to 70%, from 70% to 80%, from 80% to 90%, from 90% to 100%, from 1% to 50%, from 50% to 100%, 90%, 95%, 100%, etc.

Cellular subpopulations of cells will vary in the common or shared aspects or characteristics which define particular subpopulations. In some instances, aspects which may define a cellular subpopulation include but are not limited to, e.g., cell size, cell shape, cell granularity, cell opacity, cell nuclear to cytoplasmic ratio, cellular contents (e.g., the presence or absence or amount of particular organelles or intercellular biomolecules or compounds (e.g., nucleic acid content, lipid content, carbohydrate content, etc.)), intercellular chemistry (e.g., intercellular pH), cellular surface contents (e.g., the presence or absence or amount of particular cell membrane components (e.g., cell surface proteins, cell surface lipids, cell surface carbohydrates, etc.)). In some instances, a cell subpopulation may be defined by the presence or absence or level of, including expression level of, or change in one or more particular biomarkers. In some embodiments, cells of a subpopulation having some level of expression of biomarker may be categorized based on a set threshold of biomarker expression as described elsewhere herein.

The difference in biomarker expression between two cells belonging to two different subpopulations of cells separated by a biomarker threshold, described below, or the mean difference in biomarker expression between two cell subpopulations will vary. In some instances, e.g., as measured in terms of the relative fluorescence of a particular biomarker as analyzed by flow cytometry, biomarker expression between two cells belonging to different subpopulations may range over 7 logs. For example, in some instances a cell of a first subpopulation may have a biomarker expression level, e.g., as detected using fluorescent reporters as described herein, that is different from the biomarker expression of a cell a second subpopulation by anywhere from 0.1 to $10^7$ times, including but not limited to, e.g., from 0.1 to 1 times, from 0.1 to 10 times, from 0.1 to $10^2$ times, from 0.1 to $10^3$ times, from 0.1 to $10^4$ times, from 0.1 to $10^5$ times, from 0.1 to $10^6$ times, from 1 to 10 times, from 1 to $10^2$ times, from 1 to $10^3$ times, from 1 to $10^4$ times, from 1 to $10^5$ times, from 1 to $10^6$ times, from 1 to $10^7$ times, from 10 to $10^2$ times, from 10 to $10^3$ times, from 10 to $10^4$ times, from 10 to $10^5$ times, from 10 to $10^6$ times, from 10 to $10^7$ times, from $10^2$ to $10^3$ times, from $10^2$ to $10^4$ times, from $10^2$ to $10^5$ times, from $10^2$ to $10^6$ times, from $10^2$ to $10^7$ times, from $10^3$ to $10^4$ times, from $10^3$ to $10^5$ times, from $10^3$ to $10^6$ times, from $10^3$ to $10^7$ times, from $10^4$ to $10^5$ times, from $10^4$ to $10^6$ times, from $10^4$ to $10^7$ times, from $10^5$ to $10^6$ times, from $10^5$ to $10^7$ times, and from $10^6$ to $10^7$ times.

In some instances, the number of cells having a biomarker level above or below a particular biomarker threshold level may be determined, e.g., to further determine the proportion of cells having a biomarker level above or below a particular threshold of a particular sample population. In certain instances, the size of a subpopulation of cells or the proportion cells of a particular sample population may be used in determining a TB biomarker signature and making a TB assessment. In some embodiments, the size of a single subpopulation of cells or a single proportion of cells of a particular sample population having a biomarker level above or below a particular threshold may constitute a biomarker signature. In other embodiments, the size of multiple subpopulations of cells or multiple proportions of cells of a particular sample population having biomarker levels above or below particular thresholds constitute a biomarker signature. The number of measured and/or identified subpopulations of cells of proportions of cells of a particular sample population used in producing a biomarker signature may vary and, in some instances, may range from 1 to 200, including, e.g., 1 to 100, 1 to 50, 1 to 20, 1 to 15, 1 to 10, 5 to 15, 2 to 10, 5 to 10, 7 to 10, 3 to 10, 3 to 7, 3 to 5, etc.

In some instances, in determining a TB biomarker signature one or more second subpopulations may be determined of one or more first subpopulations. For example, in some instances, a first subpopulation is determined that expresses a first biomarker above or below a particular threshold and a second subpopulation within the first subpopulation is determined that expresses a second biomarker above or below a particular threshold. Such analysis may be described in certain instances as biomarker co-expression and may be used to determine a subpopulation of cells expressing co-expressing two or more markers above or below certain threshold levels. In some instances a subpopulation may be determined that expresses a first biomarker above a certain threshold and a second marker below a certain threshold and may be described as, e.g., a cell subpopulation that is "positive" for a first marker and "negative" for a second marker. Also contemplated are subpopulations that are "double positive" or "double negative" accordingly. Such analysis is not limited to two subpopulation levels, i.e., two subpopulations, or two biomarkers and in some instances may consist of many subpopulation levels including a range of biomarkers. The number of subpopulations and biomarkers used in such analyses will vary and in some cases may be but is not limited to anywhere from 3 to 20, including e.g., 3 to 19, 3 to 18, 3 to 17, 3 to 16, 3 to 15, 3 to 14, 3 to 13, 3 to 12, 3 to 11, 3 to 10, 3 to 9, 3 to 8, 3 to 7, 3 to 6, 3 to 5, and 3 to 4. Accordingly, subpopulations may have any combination of presence or absence of biomarkers above or below particular threshold levels, including e.g., "positive" for a first biomarker, "negative" for a second biomarker and "positive" for a third biomarker, or "triple positive" or "triple negative", etc. Such analysis is not limited to distinct subpopulations and in some instances subpopulations may overlap or a subpopulation may not be entirely contained within one or more higher level subpopulations.

TB Biomarkers

In some aspects of the present disclosure, biomarkers are provided for making a TB assessment and for use in producing a biomarker signature for making a TB assessment. By "biomarker", or in some instances simply "marker", is meant any molecular, chemical, or physiological factor whose representation in a sample is associated with a clinical phenotype or clinical outcome. For example, a TB biomarker may be differentially represented in a sample of a subject having LTBI as compared to a subject with ATB, a subject having TB as compared to a healthy individual, a subject having TB as compared to a subject having a non-TB lung disease, a subject transitioning between LTBI and ATB, such as from LTBI to ATB, a subject responding to TB therapy as compared to a subject not responding to TB therapy, a subject requiring TB therapy as compared to a subject not requiring TB therapy, or a subject requiring further TB therapy as compared to a subject not requiring further TB therapy or, etc.

Specific agents that may be evaluated as biomarkers include but are not limited to, e.g., polypeptides (e.g., peptides, proteins, lipoproteins, etc.), carbohydrates, lipids, metabolites, amino acids, electrolytes, nucleic acids (e.g., DNA, mRNA, microRNA, etc.) and the like. Biomarkers useful in assessing TB or supplementing TB assessments may be associated with cells, i.e., "cellular biomarkers" or not associated with cells, i.e., "non-cell-associated biomarkers". In some instances, non-cell-associated biomarkers include soluble host biomarkers, e.g., host serum markers. By "host serum markers" is meant those markers present in a subject's serum that may be used to diagnose disease or infection, assess disease state, or monitor disease progression or treatment efficacy. In certain instances, additional biomarkers may include subject or patient characteristics, including e.g., physiological characteristics (e.g., blood volume, blood pressure, heart rate, blood pH, blood oxygen, oxygen consumption, respiratory rate, basal metabolism, body temperature, water balance, urine density, proteinuria, aminoaciduria, creatinuria, etc.) or behavioral characteristics (e.g., verbal function, vision function, olfactory function, auditory function, tactile function, memory function, mobility, etc.). The presence, absence, or level (e.g., high level or low level) of a particular additional biomarker or a change in a particular biomarker, including e.g., a change in biomarker level or biomarker expression (i.e. increased level or expression or decreased level or expression), as included in TB assessments, may be correlated with a particular TB diagnosis or clinical evaluation. Such additional biomarkers are described in greater detail below.

Those biomarkers expressed by a host, e.g., expressed by host cells or expressed on host cells, may be referred to as host biomarkers. In some instances, host biomarkers that are differentially expressed by a host infected with TB or a subject having TB disease as compared to a non-infected subject or a subject not having TB disease are referred to as TB host biomarkers. TB host biomarkers may be detected, measured, or evaluated by any convenient method, including those methods described for biomarkers previously.

Subject biomarkers useful in making an assessment of the present disclosure include, e.g., cytokines, cytokine receptors, and markers of inflammation. Cytokines and cytokine receptors are important for cell signaling to influence the behaviors of other cells but are generally not hormones or growth factors. In some instances cytokines or their receptors that are useful as biomarkers include but are not limited to chemokines, interferons, interleukins, lymphokines, tumor necrosis factor, and the like. Such cytokines are produced in a wide range of different cells including, but not limited to, immune cells, macrophages, B lymphocytes, T lymphocytes, mast cells, and the like. Such cytokines are also produced in non-immune cells or cells that are not necessarily immune cells, e.g., endothelial cells, fibroblasts, stromal cells and the like.

In certain embodiments, biomarkers of interest include markers or combinations of markers detected by the optics and/or electronics of a flow cytometer. In some instances such markers are surface antigens, e.g., proteins, expressed or displayed on the surface of a cell and used to identify a subpopulation of cells based on similar expression levels of the same marker or markers. In other instances such markers are cellular characteristics that can be detected by the optics and/or electronics of a flow cytometer, as described herein. Markers of interest include those markers described herein that show significantly different expression levels in various treatment groups, e.g., groups at various time points following the initiation of treatment, and control groups, e.g., healthy controls or controls having other lung diseases, after Bonferroni correction, those that show significantly different expression levels in various treatment and control groups by any statistical method used herein, and those that show expression trends across treatment and/or control groups regardless of statistical significance.

In some instances, biomarkers useful in determining a TB biomarker signature for diagnosing TB in a subject are those TB host biomarkers that are present above or below a threshold level in a subpopulation of cells of a cellular sample obtained from subjects suspected of having TB. For example, in some instances the level of a TB host biomarker is measured and used to determine the relative size of a subpopulation of cells of a cellular sample obtained from a subject suspected of having TB and the size of the subpopulation is compared to a healthy control reference. In some embodiments, the relative size of the subpopulation of cells having expression of the TB host biomarker above a particular threshold in subjects suspected of having TB is smaller than that of the reference standard.

As reviewed above, aspects the methods include assaying a tuberculosis (TB) activated sample from the subject for at least one of: CD154$^+$ T cells and T cells having a central memory (CM) phenotype, such as a CM1, CM2 or CM3 phenotype. As such, in some instances a specific biomarker of interest is CD154 (i.e., CD40 ligand or CD40L, Uniprot Nos. P29965 (human) or P27548 (mouse)). In addition to, or instead of, CD154, other biomarkers indicative of T-cell activation (i.e., associated with activated T-cells), may be employed, where such markers include, but are not limited to: IFN-γ, CD69, TNF-α and the like.

In addition to employing an activated T-cell biomarker, e.g., CD154, a given assay may include employing biomarkers that identify a particular subset of memory T-cells, e.g., a central memory (CM) phenotype, such as a CM1 phenotype (CD45RA$^-$, CD197(CCR7)$^+$, CD27$^+$, CD28$^+$), CM2 phenotype (CD45RA$^-$, CD197(CCR7)$^{+/-}$, CD27$^+$, CD28$^+$) or a CM3 phenotype (CD45RA$^-$, CD197 (CCR7)$^-$, CD27$^+$, CD28$^+$). Such biomarkers include, but are not limited to, CD45RA, CD197 (CCR7), CD27, CD28, CD57 and the like. In addition to, or alternatively to, CM1/CM2/CM3 identifying biomarkers, other biomarkers that may distinguish LTBI from ATB may be employed, where such biomarkers include, but are not limited to: IL-2, TNF-α, Ki-67, HLA-D4, CD-38, CXCR3, CCR6, CD161, lymphocyte/monocyte ratio, etc. In some instances, biomarkers employed in obtaining a TB biomarker signature include CD154 in addition to CD45RA, CD197(CCR7), CD27, CD28, e.g., in those embodiments where a tuberculosis (TB) activated sample from the subject is assayed for both of CD154$^+$ T cells and T cells having a central memory phenotype, such as a CM1, CM2 or CM3 phenotype. In some instances, biomarkers employed in obtaining a TB biomarker signature include CD154 in addition to one or more of IL-2, TNF-α, Ki-67, HLA-D4, CD-38, CXCR3, CCR6, CD161. In some instances, biomarkers employed in obtaining a TB biomarker signature include CD69 and/or IFN-γ, in addition to CD45RA, CD197 (CCR7), CD27, CD28, CD57. In some instances, biomarkers employed in obtaining a TB biomarker signature include CD154 in addition to CD45RA, CD197 (CCR7), CD27, CD28, as well as one or more of: CD69, IFN-γ, IL-2, TNF-α, Ki-67, HLA-D4, CD38, CXCR3, CCR6, and CD161.

TB Activated Samples

As summarized above, aspects of the methods include assaying a tuberculosis (TB) activated sample from a subject to obtain the TB biomarker signature. TB activated samples are cellular samples. Cellular samples from which a subpopulation of cells may be identified or evaluated or measured may vary and include any sample obtained from a subject that contains cells. Cellular samples may be obtained in any convenient manner and include, but are not limited to, e.g., blood, tissue biopsy, including punch biopsy, bone marrow biopsy, bronchial aspirate, cerebrospinal fluid, sputum or other body fluids. In some instances, the cellular sample employed in methods of the invention may be unprocessed or taken directly from the subject and used in analysis, including e.g., a whole blood sample. In other instances, a cellular sample may be obtained by processing a sample obtained from a patient, including e.g., isolating cells from the sample, concentrating the cells of the sample, dissociating the cells of the sample. In some instances, the cellular sample is a blood sample or a processed blood sample, including e.g., a preparation of peripheral blood mononuclear cells (PBMCs), a preparation of serum, a preparation of immune cells, etc.

In some embodiments, the cellular sample may be obtained from a naïve subject or a subject that has not had any prior medical or pharmacological intervention, e.g., not had any medical or pharmacological intervention related to a disease assessment or diagnosis or treatment, including e.g., a TB assessment or TB treatment. In some embodiments, the subject may be a treated patient or a patient that has had some amount of prior medical or pharmacological intervention, including e.g., treatment for a disorder, e.g., a lung disorder, or an infection, e.g., a TB infection, or TB treatment, including e.g., those TB treatments described herein.

Samples employed in embodiments of the methods are TB activated samples. By TB activated sample is meant a cellular sample that is a TB antigen-stimulated sample. Antigen stimulation may be performed before sample collection, e.g., antigen stimulation may be performed in the subject by contacting the subject with the antigen and subsequently collecting the sample after antigen stimulation, or after sample collection, e.g., antigen stimulation may be performed in culture after the cells of the sample have been isolated from the subject. Antigen stimulation is performed using any convenient antigen including *Mycobacterium tuberculosis* (MTB) antigens. Specific MTB antigens that may be employed include, but are not limited to: ESAT-6, CFP-10, MTB66, etc.

Where desired, a sample from a subject may further be contacted with a T-cell co-stimulatory reagent in producing the TB activated sample. Any convenient T-cell co-stimulatory reagent may be employed, wherein such reagents may include one or more T-cell stimulatory agents, including but not limited to, specific binding members, e.g., antibodies or binding fragments thereof, to one or more of: CD28, CD49d, and the like. Commercially available T-cell co-stimulatory reagents that may be employed in preparing a TB activated cellular sample include, but are not limited to: BD Biosciences' CD28/CD49d Costimulatory Reagent (a mouse monoclonal antibody (clone L25, L293) generated using CD49d, CD28, IA4, Tp44, ITGA4, CD28 molecule, Integrin, alpha 4 (antigen CD49D, alpha 4 subunit of VLA-4 receptor) as the antigen); CD28 and CD49d together or alone and the like.

Where desired, a sample may be contacted with one or more additional reagents. For example, a sample may be contacted with secretion inhibitor. Any convenient secretion inhibitor may be employed, where examples of secretion inhibitors include, but are not limited to: Brefeldin-A (BFA), Monensin, and the like.

Where desired, a biomarker detection reagent may be combined with the sample during preparation of the TB activated sample. For example, a T-cell activation biomarker detection reagent may be combined with the initial sample obtained from the subject during preparation of the TB activated sample. As reviewed above, T-cell activation biomarkers include CD154, IFN-γ, CD69, TNFα and the like, where examples of reagents that may be employed to detect these biomarkers are described in greater detail below. For example, where CD154 is assayed, a labeled CD154 specific binding member, e.g., a fluorescently labeled CD154 antibody, may be combined with the sample during TB activated sample preparation.

In preparing the TB activated sample, the initial sample is combined with the TB activator, such as an MTB antigen (e.g., as described above) and any other desired reagents, e.g., co-stimulatory reagents, secretion inhibitors, biomarker detection reagents, etc., and maintained for a period of time and under conditions sufficient for the desired TB activated sample to be produced. In preparing the TB activated sample, the reagents and samples may be contacted and combined at a temperature ranging from 15 to 50, such as from 20 to about 40° C., e.g., 35 to 40° C., such as 37° C. Contact may be performed with mixing or agitation, e.g., with vortexing etc., to provide for sufficient combination of the reagents and the sample. The resultant reaction mixture may then be maintained or incubated for a period of time sufficient to activate the sample. In some instances, the reaction mixture is incubated at a temperature ranging from 15 to 50, such as from 20 to about 40° C. e.g., 35 to 40° C., such as 37° C., for a period of time ranging from about 30 minutes to 72 hours, such as 3 hour to 36 hours, including 6 hour to 24 hours. Following the above incubation step, the resultant TB activated sample may be assayed immediately or stored for assay at a later time. If stored, in some embodiments the sample is stored at a reduced temperature; e.g., on ice.

Following preparation of the TB activated sample, the TB activated sample may be treated to lyse red blood cells. Any convenient lysing agent may be employed, including but not limited to, ammonium chloride, a lysis buffer, etc., where suitable lysis buffers are commercially available.

In certain embodiments, the methods may include fixing the sample, for example, before contacting the sample with one or more specific binding members. The cells of the sample may be fixed through exposure to any of a number of cell fixing agents (i.e., fixation reagents), such as paraformaldehyde, glutaraldehyde, methanol, acetone, formalin, or any combination thereof. Other fixatives and fixation methods may be employed, as desired. Fixation time may vary, and in some instances ranges from 1 minute and 1 hour, such as 5 minutes and 30 minutes. The temperature at which fixation takes place may vary, and in some instances the temperature ranges from −30° C. to 40° C.

In certain aspects, the sample may be treated with a permeabilization agent prior to contacting the sample with an intracellular marker specific binding member. Permeabilization may allow an intracellular marker specific binding member to enter cells in the sample. Permeabilization may take place before, after, or at the same time as the fixation previously described. The cells of the sample may be permeabilized through exposure to any of a number of cell permeabilizing agents, such as methanol, acetone or a detergent (e.g., triton, NP-40, saponin, tween 20, digitonin, leucoperm, etc.), or a combination thereof. Permeabilization time may vary, and in some instances ranges from 1 minute to 1 hour, such as from 5 minutes to 30 minutes. The temperature at which permeabilization takes place may vary, and in some instances the temperature may range from 0° C. to 50° C. In certain aspects, the cells in the cellular sample are not permeabilized prior to when the sample is contacted with the cell surface marker specific binding member.

In some instances, samples used in making a TB assessment are fresh samples, e.g., samples collected from subject within 1 to 5 days, including e.g., within 5 days, within 4 days, within 3 days, within 2 days, and within 1 day. In some instances, samples used in making a TB assessment are previously collected samples. Previously collected samples may be stored under appropriate conditions before analysis and may be processed, e.g., partitioned, including e.g., the removal or partitioning of a particular component or portion of a blood sample, or unprocessed prior to storage. In some instances, appropriate storage conditions include refrigerator storage, including e.g., storage below room temperature but above freezing temperatures, including e.g., storage between 21° C. and 1° C., between 10° C. and 1° C., between 10 and 4° C., etc. Refrigeration may, in some instances, include sample storage on ice. In some instances, appropriate storage conditions include freezing conditions, including e.g., freezing at temperatures ranging from 0° C. to −200° C., including, e.g., storage at 0° C. to −10° C., 0° C. to −20° C., −20° C. to −50° C., −20° C. to −60° C., −20° C. to −70° C., −60° C. to −80° C., −60° C. to −90° C., −60° C. to −100° C., −60° C. to −110° C., −60° C. to −120° C., −120° C. to −130° C., −120° C. to −140° C., −120° C. to −150° C., −120° C. to −160° C., −120° C. to −170° C., −120° C. to −180° C., −120° C. to −190° C., −120° C. to −200° C., etc.

Biomarker Detection

As reviewed above, aspects of the methods include assaying the TB activated sample for one or more biomarkers in order to obtain a TB biomarker signature for the sample. In certain instances, biomarker detection involves the evaluation or assessment of the level of a biomarker. The level of a biomarker may, in some instances, refer to the level of a biomarker. By "level of a biomarker" or "biomarker level" is meant the level at which a particular biomarker is present in a sample and may include but is not limited to, e.g., the level of a soluble biomarker in a bodily fluid, the level of a cellular biomarker present in a sample, the level of a cellular biomarker present within a cell, the level of a cellular biomarker present on a cell, the level of a cellular biomarker present on the surface of a cell, the level of a cellular biomarker present on a cellular membrane. In some instances, level of a biomarker may refer to the relative abundance of RNA, DNA or protein abundances or activity levels. Level of a biomarker may be evaluated or determined or measured by any convenient method including but not limited to, e.g., gene-chips, gene arrays, beads, multiplex PCR, quantitiative PCR, run-on assays, Northern blot analysis, Western blot analysis, protein expression, fluorescence activated cell sorting (FACS), enzyme linked immunosorbent assays (ELISA), chemiluminescence studies, enzymatic assays, or any other method, apparatus and system for the determination and/or analysis of expression that are readily commercially available.

In certain embodiments, biomarker detection and/or measurement of biomarker levels is performed using flow cytometry. Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when quantifying and/or sorting cells by any marker present on or in the cell, typically are fluorescently-tagged antibody preparations or fluorescently-tagged ligands for binding to antibodies or other antigen-, epitope- or ligand-specific agent, such as with biotin/avidin binding systems or fluorescently-labeled and optionally addressable beads (e.g. microspheres or microbeads). The markers or combinations of markers detected by the optics and/or electronics of a flow cytometer vary and in some cases include but are not limited to: cell surface markers, intracellular and nuclear antigens, DNA, RNA, cell pigments, cell metabolites, protein modifications, transgenic proteins, enzymatic activity, apoptosis indicators, cell viability, cell oxidative state, etc.

In certain instances, flow cytometry is performed using a detection reagent, e.g., a labeled specific binding member, such as a fluorochrome-labeled antibody, e.g., a monoclonal antibody, that specifically binds to a biomarker antigen of interest of a cell, e.g., a biomarker present on the surface of a cell. As reviewed above, biomarkers that may be assayed in a given embodiment include one or more of, including two or more of, e.g., three or more of, such as four or more of CD154, CD45RA, CD197(CCR7), CD27, CD28, CD69, IFN-γ, IL-2, TNF-α, Ki-67, HLA-D4, CD-38, CXCR3, CCR6, and CD161. Additional biomarkers that may be assayed include T-cell identifying biomarkers, e.g., CD3, CD4 and/or CD8, etc.

A variety of specific binding members that specifically bind to the biomarkers of interest in a given assay are suitable for embodiments of the subject invention. In any of the above embodiments, one or more of the specific binding members (e.g., binding members for CD154, CD45RA, CD197(CCR7), CD27, CD28, CD69, IFN-γ, IL-2, TNF-α, Ki-67, HLA-D4, CD-38, CXCR3, CCR6, CD161, CD3, CD4 and/or CD8) may include a specific binding domain. The terms "specific binding", "specific for", "specifically binds" and the like, refer to the preferential binding of a the binding member to a particular target (e.g., to a cell type, to a specific extracellular or intracellular marker, etc.). The specific binding domain may bind (e.g., covalently or non-covalently) to a specific epitope on or within the cell. In certain aspects, a specific binding domain non-covalently binds to a target. In such instances, the specific binding domain association with the binding target (e.g., CD77) may be characterized by a KD (dissociation constant) of $10^{-5}$ M or less, $10^{-8}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. A variety of different types of specific binding domains may be employed. Specific binding domains of interest include, but are not limited to, antibodies, proteins, peptides, haptens, nucleic acids, etc. The term "antibody" as used herein includes polyclonal or monoclonal antibodies or fragments thereof that are sufficient to bind to a target of interest. The term "antibody" also includes antibody fragments, such as, monomeric Fab fragments, monomeric Fab' fragments, or dimeric F(ab)'2 fragments. Also within the scope of the term "antibody" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

As indicated above, the detection reagents are labeled. By labeled is meant that the detection reagents include a detectable moiety, such as a fluorescent moiety. For example, a given specific binding member may be detectably labeled with a colored dye, a phosphorescent label, a fluorescent label, a mass tag, a radioactive label, or any other suitable label. For example, the label domain may be a fluorescent label detectible based on, for example, fluorescence emission maxima, fluorescence polarization, fluorescence lifetime, light scatter, or a combination thereof. In certain aspects, the label domain may be a fluorophore (i.e., a fluorescent label, fluorescent dye, etc.). Fluorophores can be selected from any of the many dyes suitable for use in analytical applications (e.g., flow cytometry, imaging, etc.).

Examples of fluorophores that may be incorporated into the microparticles include, but are not limited to, 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5', 5'''-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine, IR144, IR1446, Green Fluorescent Protein (GFP); Reef Coral Fluorescent Protein (RCFP); Lissamine™ Lissamine rhodamine, *Lucifer* yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. The fluorescent label may be distinguishable based on fluorescence emission maxima, and optionally further based on light scatter or extinction. Detection reagents useful in flow cytometry, e.g., including but not limited to antibodies, may be created in the laboratory using well established methods and are commercially available for e.g., BD (Franklin Lakes, N.J.) and BD Biosiences (San Jose, Calif.).

In some instances, the fluorophore (i.e., dye) is a polymeric dye (e.g., a fluorescent polymeric dye). Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. The structural characteristics of the polymeric dyes can have an effect on the fluorescence properties of the molecules.

Any convenient polymeric dye may be utilized in the subject devices and methods. In some instances, a polymeric dye is a multichromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multichromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer), and the like. In some instances, these energy transfer mechanisms are relatively short range; that is, close proximity of the light harvesting multichromophore system to the signaling chromophore provides for efficient energy transfer. Under conditions for efficient energy transfer, amplification of the emission from the signaling chromophore occurs when the number of individual chromophores in the light harvesting multichromophore system is large; that is, the emission from the signaling chromophore is more intense when the incident light (the "excitation light") is at a wavelength which is absorbed by the light harvesting multichromophore system than when the signaling chromophore is directly excited by the pump light.

The multichromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via Forster energy transfer.

Polymeric dyes of interest include, but are not limited to, those dyes described by Gaylord et al. in U.S. Publication Nos. 20040142344, 20080293164, 20080064042, 20100136702, 20110256549, 20120028828, 20120252986 and 20130190193, the disclosures of which are herein incorporated by reference in their entirety; and Gaylord et al., *J. Am. Chem. Soc.*, 2001, 123 (26), pp 6417-6418; Feng et al., *Chem. Soc. Rev.*, 2010, 39, 2411-2419; and Traina et al., *J. Am. Chem. Soc.*, 2011, 133 (32), pp 12600-12607, the disclosures of which are herein incorporated by reference in their entirety.

As mentioned above, TB activated sample is combined with labeled biomarker detection reagents under conditions sufficient to produce a labeled sample. Contact of the sample with the labeling reagents is performed under incubation conditions that provide for binding of labeling reagents to their respective biomarkers, if present, in the sample. In some instances, the reaction components and samples are contacted and combined at a temperature ranging from 15 to 50, such as from 20 to about 40° C. Contact may be performed with mixing or agitation, e.g., with vortexing etc., to provide for sufficient combination of the reaction components and the sample. The resultant reaction mixture may then be maintained or incubated for a period of time prior to flow cytometric analysis. In some instances, the reaction mixture is incubated at a temperature ranging from 15 to 50, such as from 20 to about 40° C. for a period of time ranging from about 30 minutes to 72 hours, such as 1 hour to 24 hours, including 1 hour to 3 hours. Following the above incubation step, the sample may be assayed immediately or stored for assay at a later time. If stored, in some embodiments the sample is stored at a reduced temperature; e.g., on ice.

A labeled cellular sample, e.g., as described above, may then be loaded into a flow cytometer, e.g., by loading the entire sample or a portion of the unmodified sample into the flow cytometer or by first isolating the cells from the cellular sample using cell isolation methods known in the art or described herein and re-suspending the isolated cells in a suitable buffer, e.g., running buffer. The cells loaded into the flow cytometer are run through the flow cytometer, e.g., by flowing cell containing buffer or liquid sample through the flow cell of the flow cytometer. The flow cytometer detects events as the cell passes one or more detection areas of the flow cytometer. For example, the flow cytometer may detect fluorescence emitted from a fluorochrome of a detection reagent upon excitation of the fluorochrome with a particular wavelength of light. In some instances, the flow cytometer detects the relative intensity of a particular signal, e.g., fluorescence of a particular detection reagent, of a particular cell, e.g., the quantify the level of a marker present on the surface of the cell and/or to qualitatively categorize the cell, e.g., as a cell that is positive for a particular marker or a cell that is negative for a particular marker. Detected events are counted or otherwise evaluated by the flow cytometer without or without input from an operator and used to determine, e.g., the total number of cells, the number or proportion of cells bound to a particular detection reagent, the overall presence or amount of a particular feature of a cell population, etc.

In some instances, a biomarker threshold is determined by making a comparison of the subject biomarker. For example, a first cell population known to have a high level of Biomarker X is measured, e.g., on a flow cytometer, and compared to a second cell population, known to have a low level of Biomarker X and the comparison is used to determine a threshold level that may be used to categorize cells as either having a low or a high level of expression of Biomarker X.

In some instances, a biomarker threshold is determined by making a comparison of the levels of a biomarker within a population of cells, e.g., a population of cells of unknown levels of Biomarker X or a population of cells suspected of containing subpopulations of cells having different levels of Biomarker X. For example, the level of Biomarker X is measured on a flow cytometer of at least a sufficient number of cells such that the measurements may be plotted, e.g., on a histogram, and separation between two or more subpopulations of cells is revealed based on individual cell levels of Biomarker X. Accordingly, the flow cytometer operator may then determine a threshold level between the subpopulations that may be used to categorize cells as belonging to a particular subpopulation, e.g., a subpopulation having a low level of Biomarker X or a subpopulation having high level of Biomarker X.

In some instances, the biomarker threshold is based on the limit of detection of the flow cytometer. For example, cells of a population of cells may be identified as having a particular biomarker (i.e. being positive for a particular biomarker) if the cells have any detectable level of a particular biomarker. Likewise, cells of a population of cells may be identified as not having a particular biomarker (i.e. being negative for a particular biomarker) if the cells do not have a detectable level of a particular biomarker. Accordingly, the detection level of the flow cytometer may be used to determine the biomarker threshold.

In some instances, the biomarker threshold is based on previously determined biomarker levels (i.e. reference biomarker levels), e.g., from previously performed control experiments or previously acquired reference levels. For example, biomarker levels determined in previously analyzed patient samples, e.g., from TB patients and healthy patients, LTBI patients, ATB patients, etc., may be used to determine biomarker threshold levels. In some instances, biomarker levels expected of cells obtained from healthy subjects may be used to determine normal biomarker levels such that a biomarker threshold that is representative of the normal biomarker range may be determined. In such instances, biomarker levels outside, i.e., above or below, the normal biomarker range is considered to be either above or below the particular biomarker threshold. In some instances, use of such previously determined biomarker levels or previously determined threshold levels allows analysis of cells and the identification of cellular subpopulations in the absence of a control or reference cellular sample.

In certain embodiments, an assessment is made based on a biomarker signature that includes biomarkers in addition to the biomarkers specifically described herein. In certain instances, such additional biomarkers may be referred to as "non-TB host biomarkers" or simply "additional biomarkers". Any convenient non-TB host biomarkers or additional biomarkers useful in making an assessment of a subject suspected of having TB or known to have TB, including for e.g., biomarkers used to assess general health or a non-TB related condition or disease may find use in the assessments described herein.

In certain embodiments where an assessment is made based on a TB biomarker signature that includes biomarkers in addition to TB host biomarkers as described herein, such additional biomarkers may include gene expression changes, e.g., gene expression changes within host cells, e.g., host blood cells, identified by assaying the relative amount of mRNA for particular genes in cells obtained from different treatment groups or patient groups. For example, genes that are differentially expressed in pulmonary TBs patients assayed at various points of treatment, e.g., at diagnosis and during treatment, including but not limited to those described by Cliff et al. (2013) *J. Infect. Dis.* 207(1):18-29, the disclosure of which is incorporated herein by reference.

In some instances, certain biomarkers have characteristics that justify their exclusion from a particular biomarker signature or TB assessment. Characteristics of biomarkers that may justify exclusion from a biomarker signature include but are not limited to, e.g., high baseline expression of the biomarker, low baseline expression of the biomarker, variable expression of the biomarker in control samples, etc. For example, in some instances, biomarkers useful in determining a biomarker signature for monitoring TB treatment progression in a patient during TB treatment specifically excludes host TB biomarkers that are expressed at high levels. For example, in some instances biomarkers that show a statistically significant difference between two treatment groups may be excluded from a biomarker signature used to make a TB assessment, e.g., because such difference is not biologically meaningful. Host TB biomarkers that are expressed at high levels may vary and in some instances include but are not limited to those markers that are present in 85% to 100% of the measured population of cells, including e.g., 86% to 100%, 87% to 100%, 88% to 100%, 89% to 100%, 90% to 100%, 91% to 100%, 92% to 100%, 93% to 100%, 94% to 100%, 95% to 100%, 96% to 100%, 97% to 100%, 98% to 100%, 99% to 100%, 85% to 99%, 90% to 99%, and 95% to 99%.

Assaying a TB activated sample, e.g., as described above, results in the production of TB biomarker signature. As reviewed above, the TB biomarker signature is made up biomarker data for two more biomarkers, i.e., a plurality of biomarkers. In embodiments, the TB biomarker signature is made up of at least one of CD154 data and CM phenotype data, e.g., CM1/CM2/CM3 phenotype data, e.g., CD45RA, CD197 (CCR7), CD27, CD28 data. In embodiments, the TB biomarker signature is made up of CD154, CD45RA, CD197 (CCR7), CD27, CD28 data. A given TB biomarker signature may include data for one or more additional markers, such as those specifically described above, including T-cell identification data, e.g., CD3, CD4 and/or CD8 data, etc.

Deriving a TB Assessment from a TB Biomarker Signature

The subject disclosure describes biomarker evaluations and/or measurements that are used to produce a biomarker signature, which signature may be used in making a TB assessment. The use of biomarker evaluations and/or measurements and produced biomarker signatures in making TB assessments will vary as described herein. In certain embodiments, TB assessments of subjects, e.g., for use in diagnosing TB or clinically monitoring TB in a subject, are performed by detecting the levels of host biomarkers, e.g., host biomarkers including TB biomarkers present on the surface of cells, obtained from the subject. For example, the level of a host biomarker used in making an assessment of a subject may be measured and compared to a particular biomarker threshold, e.g., to determine whether the biomarker is present above a particular threshold level or below a particular threshold level. In certain instances, the number or proportion of cells of a sample having a biomarker level above or below a particular biomarker threshold level is determined, e.g., to identify a particular subpopulation or multiple subpopulations or produce a biomarker signature, and used in making the assessment.

The use of biomarker signatures in making TB assessments will vary and may depend on the particular subject or patient population and the purpose of the particular TB assessment. Biomarker signatures may be compared to reference biomarker signatures to guide diagnosis or treatment or monitoring of treatment or monitoring of disease progression and the particular aspects of the TB assessment may depend on the medical history or treatment circumstances of the particular subject.

Treatment

In certain instances, TB assessments as described herein may be used to monitor TB treatment, e.g., TB treatment of subjects with latent TB infection or subjects with TB disease. Treatments of TB vary, as described below, during which time monitoring may be performed at some regular or variable frequency, and in some cases may include taking one or more TB affective drugs for a period of time, e.g., ranging from one month to many years, including but not limited to, e.g., 1 to 12 months, 2 to 12 months, 3 to 12 months, 4 to 12 months, 5 to 12 months, 6 to 12 months, 1 to 9 months, 2 to 9 months, 3 to 9 months, 4 to 9 months, 5 to 9 months, 6 to 9 months, 9 months to 12 months, 1 year to 2 years, 1 year to 3 years, etc. In some instances, one or more TB assessments are performed at or near the planned end of treatment including but not limited to on the last planned day of treatment or within 1 day to 1 month of the planned last day of treatment, including e.g., within 1 to 2 days, within 2 to 3 days, within 3 to 5 days, within a week, within 2 weeks, within 3 weeks, within a month, etc., in order to determine whether treatment should be stopped as planned. For example, in some instances a TB assessment performed at or near the planned end of treatment (i.e. an end-of-treatment assessment) may indicate that treatment should not be stopped as planned, e.g., the TB assessment may indicate, e.g., a higher than anticipated state of TB infection or TB disease such that a medical professional would determine that treatment should be continued. In other instances, e.g., an end-of-treatment assessment may indicate that treatment should be stopped sooner than planned, e.g., the TB assessment may indicate, e.g., a lower than anticipated state of TB infection or TB disease such that a medical professional would determine that treatment should be stopped.

TB assessments may be employed to determine treatment regiments for a subject, and where desired, aspects of the methods may further include administering the determined treatment regimen to the subject. In certain embodiments, persons with latent TB infection may remain untreated and the TB infection may be monitored using the assessments described herein, e.g., an untreated TB infected subject may be monitored in order to detect or predict the development of TB disease. In other instances, persons with latent TB infection may be treated, e.g., to prevent the development of TB disease, and the TB infection may be monitored using the assessments described herein, e.g., a TB infected subject undergoing treatment may be monitored in order to detect or predict the development of TB disease. When used for monitoring, e.g., monitoring TB infection or TB disease, the frequency of TB assessments may vary and may range, e.g., from frequencies of daily to annually, including but not limited to daily, every other day, every two days, twice weekly, weekly, once every other week, once every three weeks, monthly, once every two months, quarterly, once every four months, once every five months, once every six months, once every seven months, once every eight months, once every nine months, once every ten months, once every eleven months, annually, etc. In some instances, the frequency of monitoring may be based on a subjects risk of developing TB disease, e.g., subjects with higher risk of developing TB disease, e.g., immunocompromised subjects, may undergo monitoring with high assessment frequency and subjects with normal immune function, e.g., non-immunocompromised subjects, may undergo monitoring with assessment low frequency.

Current treatments of TB vary and particular TB treatment regimens are chosen by medical practitioners depending upon a number of clinical factors including but not limited to, e.g., characteristics of the particular subject undergoing therapy, characteristics of the particular TB being treated, e.g., TB disease, latent TB, drug-resistant TB, etc. For example, those current treatments suggested by the Center for Disease Control (CDC) for latent TB and TB disease include those described in Table 1 and Table 2 below:

TABLE 1

Latent TB Infection Treatment Regimens

| Drugs | Duration | Interval | Minimum doses |
|---|---|---|---|
| Isoniazid | 9 months | Daily | 270 |
|  |  | Twice weekly* | 76 |
| Isoniazid | 6 months | Daily | 180 |
|  |  | Twice weekly* | 52 |
| Isoniazid and Rifapentine | 3 months | Once weekly* | 12 |
| Rifampin | 4 months | Daily | 120 |

*Use Directly Observed Therapy (DOT)

TABLE 2

Basic TB Disease Treatment Regimens

| Preferred Regimen | Alternative Regimen | Alternative Regimen |
|---|---|---|
| Initial Phase Daily INH, RIF, PZA, and EMB* for 56 doses (8 weeks) | Initial Phase Daily INH, RIF, PZA, and EMB* for 14 doses (2 weeks), then | Initial Phase Thrice-weekly INH, RIF, PZA, and EMB* for 24 doses (8 weeks) |

TABLE 2-continued

Basic TB Disease Treatment Regimens

| Preferred Regimen | Alternative Regimen | Alternative Regimen |
|---|---|---|
| Continuation Phase Daily INH and RIF for 126 doses (18 weeks) or Twice-weekly INH and RIF for 36 doses (18 weeks) | twice weekly for 12 doses (6 weeks) Continuation Phase Twice-weekly INH and RIF for 36 doses (18 weeks) | Continuation Phase Thrice-weekly INH and RIF for 54 doses (18 weeks) |

Abbreviations: isoniazid (INH), rifampin (RIF), pyrazinamide (PZA), ethambutol (EMB).
*EMB can be discontinued if drug susceptibility studies demonstrate susceptibility to first-line drugs.
Note:
A continuation phase of once-weekly INH/rifapentine can be used for HIV negative patients who do not have cavities on the chest film and who have negative acid-fast bacilli (AFB) smears at the completion of the initial phase of treatment.

In certain embodiments, the methods may include a determination that an aggressive tuberculosis treatment is indicated for a subject. An aggressive tuberculosis treatment may include administering a combination of more than two antibacterial agents, optionally in combination with a corticosteroid such as dexamethasone. In certain embodiments, the aggressive tuberculosis treatment may include administering a combination of isoniazid, rifampicin, pyrazinamide, and ethambutol. In certain embodiments, an aggressive tuberculosis treatment may include administering meropenem and clavulanic acid in combination with one or more additional antibiotic agents.

In some instances, the methods may include a determination that a less aggressive tuberculosis treatment is indicated for a subject. In certain embodiments, the less aggressive tuberculosis treatment is only one or not more than a combination of two antibacterial agents. In certain embodiments, the less aggressive tuberculosis treatment is a combination of only isoniazid and rifampicin. In certain embodiments, the measurement, quantification, or indication is recorded on a computer readable medium. In certain embodiments, the measurement, quantification, or indication is communicated to a medical professional or the subject.

The term "antibacterial" or "antibiotic" agent refers to molecules that may either kill or inhibit the growth of bacteria. In certain embodiments, the antibiotic is selected from the group comprising of sulfonamides, diaminopyrimidines, quinolones, beta-lactam antibiotics, cephalosporins, retracyclines, nitrobenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones. In further embodiments, these antibiotics include but are not limited to sulphadiazine, sulfones-[dapsone (DDS) and paraaminosalicyclic (PAS)], sulfanilamide, sulfamethizole, sulfamethoxazole, sulfapyridine, rrimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam) oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, imidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin, polymyxin B, polymyxin B sulfate, procain, spectinomycin, tinidazole, trimethoprim, ramoplanin, teicoplanin, vancomycin, trimethoprim, sulfamethoxazole, nitrofurantoin, pro-drugs or alternative salts thereof. In certain embodiments, the aggressive treatment comprises liposomes including agents selected from phosphatidylcholine (PC), L-a phosphatidic acid (PA) and cholesterol containing 4-(5-pentadecyl-1,3,4-oxadiazol-2-yl)pyridine.

In some instances TB treatment may include a continuation phase. In certain instances the continuation phase of treatment is given for a period of time following an initial phase of treatment, e.g., for 4 or 7 months. The length of the continuation phase may vary and may depend upon particular patient characteristics. For example, a 7-month continuation phase is recommended for particular patient groups, including e.g., patients with cavitary pulmonary tuberculosis caused by drug-susceptible organisms and whose sputum culture obtained at the time of completion of 2 months of treatment is positive; patients whose initial phase of treatment did not include PZA; and patients being treated with once weekly INH and rifapentine and whose sputum culture obtained at the time of completion of the initial phase is positive. In certain embodiments, monitoring of treatment through the use of TB assessments described herein may be performed during such a continuation phase. In other instances monitoring of treatment through the use of TB assessments described herein may be stopped before or during a continuation phase.

The end of TB treatment is commonly determined by the completion of a particular treatment regimen, e.g., a particular drug regimen including, e.g., a number of drug doses ingested over a given period of time. In certain instances TB treatment regimens, including the determined end of TB treatment, are modified according to particular patient characteristics, including, e.g., HIV infection, drug resistance, pregnancy, patient age, etc. In certain instances the end of TB treatment may be determined based on TB assessments described herein in conjunction with the end of a particular treatment regimen, e.g., the end of TB treatment determined by a particular treatment regimen may be altered based on the results of a particular TB assessment. In certain instances the end of the TB treatment may be determined based on a TB assessment described herein independently of any particular treatment regimen, e.g., the end of TB treatment may be determined essentially by one or more TB assessments as described herein. In some instances, such TB assessments useful in determining and/or confirming the end of TB treatment include but are not limited to those assessments described herein end-of-treatment assessments and post-treatment assessments.

In some instances, monitoring of TB treatment includes one or more post treatment assessments or follow-up assessments that are preformed after treatment has been stopped, e.g., to detect a relapse of TB disease or TB infection. The timing and frequency of follow-up assessments will vary and will depend on characteristics of the TB infection (e.g., whether the patient has a latent infection or TB disease), characteristics of the treatment regimen (e.g., the duration of the treatment), characteristics of the subjects medical history (e.g., whether the subject has or has had other lung diseases or treatments), the subject's relative risk of relapse (e.g., whether the subject is immunocompromised, at an increased risk of becoming immunocompromised, or non-immuno-compromised), and other considerations (e.g., the availability of the subject for further follow-up testing, the subject's age, quality of life considerations, etc.). In some instances one or more follow-up assessments may be performed in a period after the last treatment ranging from days to years including but not limited to, e.g., from 2 days to 10 years, from 2 days to 5 years, from 2 days to 2 years, from 2 days to 1 year, from 2 days to 9 months, from 2 days to 6 months, from 2 days to 3 months, from 2 days to 2 months, from 2 days to 1 month, from 2 days to 3 weeks, from 2 days to 2 weeks, from 2 days to 1 week, from 1 to 2 weeks, from 1 to 3 weeks, from 1 week to 1 month, from 1 week to 2 months, from 1 to 6 months, from 1 to 5 months, from 1 to 4 months, from 1 to 2 years, from 1 to 3 years, from 1 to 4 years, from 1 to 5 years, from 1 to 6 years, from 1 to 7 years, from 1 to 8 years, from 1 to 9 years, from 1 to 10 years, etc. As discussed above, the frequency of follow-up assessments may vary and in some instances may range, e.g., from frequencies of daily to annually, including but not limited to daily, every other day, every two days, twice weekly, weekly, once every other week, once every three weeks, monthly, once every two months, quarterly, once every four months, once every five months, once every six months, once every seven months, once every eight months, once every nine months, once every ten months, once every eleven months, annually, etc. In some instances, follow-up assessments are performed indefinitely, e.g., for the rest of a subject's life, and the need for such indefinite follow-up may depend on various clinical factors and may be necessary, e.g., due to declining immune function, e.g., due to age related immune system decline.

The present disclosure provides methods for making TB assessments of subjects, such as diagnosing and clinically monitoring TB in a subject, by detecting the levels of one or more biomarkers, including e.g., TB biomarkers, e.g., TB host biomarkers present on the surface of cells obtained from the subject.

In some instances a subject in need of a TB assessment may be a mammal, e.g., a human, suspected of recently having been infected with TB bacteria, e.g., following a TB exposure, e.g., association or contact with a TB infected person or animal or following contact with materials suspected or known to contain TB bacteria, including e.g., TB patient samples or materials known to have been in contact with a TB patient. In some instances, a TB exposure may also include indirect association with a TB infected person, including e.g., occupying a location known to have been previously occupied by a TB infected person or having contact or association with a person known to have had contact or association with a TB infected person. In certain instances an infection or an exposure may be considered recent when the infection or exposure occurs within a time period of less than 1 year from the known or suspected infection or exposure, including but not limited to, e.g., less than 6 months, less than 5 months, less than 4 months, less than 3 months, less than 2 months, less than 1 month, less than 3 weeks, less than 2 weeks, less than 1 week, 1 week, 6 days, 5 days, 4 days, or 3 days.

In some instances a subject in need of a TB assessment may be a person suspected or known to have a latent TB infection or a person suspected or known to have TB disease. A subject infected with TB bacteria may or may not develop TB disease, i.e., a TB infected individual may become symptomatic, developing TB disease or remain asymptomatic for some time thus having a latent TB infection. In TB disease, TB bacteria become active, either in a newly infected individual or an individual with a latent TB infection, when the individual's immune system fails to suppress TB bacterial growth. TB disease may be defined as a TB infection in which TB bacteria are actively multiplying in a host's body. Subjects with TB disease are generally symptomatic and infectious.

A person suspected of or known to have a latent TB infection may be described herein as a latent TB patient or a latent TB infected subject. A latent TB patient may have a latent TB infection for any period of time and the development of TB disease from latent TB depends on the presence or absence of various risk factors. Many people with latent TB infection never develop TB disease. Some people develop TB disease within weeks after becoming infected and others develop TB disease years after latent infection, e.g., after becoming immunocompromised, e.g., from a secondary infection, e.g., from a secondary HIV infection. In immunocompromised people the risk of developing TB disease is much higher than for non-immunocompromised people, i.e., those with normal immune systems. As such, in some instances a subject in need of a TB assessment may be a subject that has recently had an immune compromising event, e.g., a recent infection with an immune compromising agent including e.g., agents that cause immune compromising diseases, e.g., HIV, or recently discovered to be infected with an immune compromising agent.

Based on the cumulative presence or absence of particular risk factors a subject may have a high, normal, or low risk for developing TB disease. Risk factors that increase a subject's chances of developing TB disease, i.e. risk factors that would indicate high risk, include but at not limited to recent infection with TB bacteria, age related weak immune systems (e.g., babies, young children, and elderly individuals), other medical conditions that weaken the immune system (e.g., HIV infection, substance abuse, silicosis, diabetes mellitus, severe kidney disease, low body weight, organ transplants, head and neck cancer, etc.), concurrent medical treatment that weaken the immune system (e.g., immunosuppressive drugs, corticosteroids, anti-rejection drugs following organ transplant, radiation therapy, chemotherapy, treatments for rheumatoid arthritis, treatments for Crohn's disease, etc.).

In some instances, subjects in which a TB assessment is made may or may not have other lung diseases, e.g., another lung in addition to TB or another lung disease in place of TB, e.g., another lung disease that may be mistaken for TB. Such other lung diseases include but are not limited to: Acute Bronchitis, Acute Respiratory Distress Syndrome (ARDS), Asbestosis, Asthma, Bronchiectasis, Bronchiolitis, Bronchiolitis Obliterans Organizing Pneumonia (BOOP), Bronchopulmonary Dysplasia, Byssinosis, Chronic Bronchitis, Coccidioidomycosis (Cocci), COPD, Cryptogenic Organizing Pneumonia (COP), Cystic Fibrosis, Emphysema, Hantavirus Pulmonary Syndrome, Histoplasmosis, Human Metapneumovirus, Hypersensitivity Pneumonitis, Influenza, Lung Cancer, Lymphangiomatosis, Mesothelioma, Middle Eastern Respiratory Syndrome, Nontuberculosis *Mycobacterium*, Pertussis, Pneumoconiosis (Black Lung Disease), Pneumonia, Primary Ciliary Dyskinesia, Primary Pulmonary Hypertension, Pulmonary Arterial Hypertension, Pulmonary Fibrosis, Pulmonary Vascular Disease, Respiratory Syncytial Virus, Sarcoidosis, Severe Acute Respiratory Syndrome, Silicosis, Sleep Apnea, and the like.

Additional TB Evaluations

In certain embodiments, a TB assessment that includes the production or analysis of a biomarker signature also includes further assessments or tests, such that production or analysis of the TB biomarker signature is one component of a more extension evaluation protocol, which extensive evaluation protocol may include, e.g., a plurality of tests. In some instances, a TB assessment may include the production or analysis of a TB biomarker signature prior to, concurrent with, or following one or more additional clinical evaluations or tests. For example, a TB assessment that includes the production or analysis of a TB biomarker signature may be performed following a conventional clinical evaluation, including but not limited to, e.g., a conventional physical examination, conventional blood work, a conventional lung function test, a conventional TB test, etc. In other embodiments, a TB assessment consists essentially of, if not only of, the production or analysis of one or more TB biomarker signatures.

Additional clinical evaluations or tests, also referred to herein as "other clinical tests" that may contribute to a TB assessment may vary and include, but are not limited to, those tests known to be useful in assessing TB infection, TB disease, other lung diseases (e.g., those described herein), or general lung function. For example, in some instances an assessment includes one or more lung function tests, including but not limited to: Forced Vital Capacity (FVC), FVC % p, Forced Expiratory Volume in 1 Second (FEV1), FEV1% (FEV1/FVC), Peak Expiratory Flow (PEF), Forced Expiratory Flow 25-75% or 25-50% (FEF 25-75% or 25-50%), Forced Inspiratory Flow 25%-75% or 25%-50% (FIF 25-75% or 25-50%), Forced Expiratory Time (FET), Tidal Volume (TV), Maximum Voluntary Ventilation (MW), Functional residual capacity (FRC), The lung carbon monoxide diffusing capacity (DLCO), and the like. Other clinical tests that may be used as part of or in combination with a TB assessment as described herein include but are not limited to computerized tomography (CT) scan, positron emission tomography (PET) scan, combined PET-CT scan, magnetic resonance imaging (MRI), sputum smear, culture, genetic testing, proteomic testing, etc. For example, in some instances, a TB assessment may include one or more CT, PET, combined PET/CT or MRI scans and analysis of such scans, e.g., as described in Skoura et al., *Int J Infect Dis.* 2015, 32:87-93; Vorster et al., *Mol Imaging Radionucl Ther.* 2015, 5; 24(1):42; Coleman et al., *Sci Transl Med.* 2014, 6(265):265ra167; Chen et al., *Sci Transl Med.* 2014 Dec. 3; 6(265):265ra166 and Vorster et al., *Curr Opin Pulm Med.* 2014, 20(3):287-93, the disclosures of which are incorporated herein by reference in their entirety.

In certain embodiments, in making a TB assessment, one or more conventional TB tests may be performed in addition to the TB assessments described herein, e.g., to confirm or disconfirm a result of a previous conventional TB test. Conventional TB tests include, e.g., TB screening tests. In certain instances, conventional TB tests may be used as a component of a comprehensive TB assessment, e.g., used in conjunction with an assessment that includes a determination of a biomarker signature as described herein, which may lead to an evaluation of TB treatment or a TB diagnosis. Conventional TB tests may be used to detect latent TB and TB disease. Any convenient TB testing method may be employed, including but not limited to, e.g., the TB skin test (TST), TB blood tests, etc. Conventional TB tests are generally given by a health care provider or local health department and may be considered as screening tests. Positive reactions to conventional TB tests generally indicate a need for further tests, e.g., to confirm TB infection or to determine whether the subject has TB disease. In some instances, further testing indicated by a positive reaction to a conventional TB test is performed using the TB assessments described herein.

In certain embodiments, a TB assessment may include a determination, assessment, or measurement of biomarkers in addition to those specific biomarkers described herein. Such additional biomarkers include those biomarkers in addition to those described herein that may be used to diagnose TB, assess TB disease state, monitor TB disease progression, evaluate TB treatment efficacy, or assess general health.

In some instances, TB assessments that include clinical monitoring, including, e.g., end of treatment assessments and follow-up assessments, may be performed to detect the occurrence of drug-resistant or multi-drug resistant TB infection, e.g., to indicate the necessity of initiation of a drug-resistant TB treatment regimen. Drug-resistant TB is caused by TB bacteria that are resistant to at least one first-line anti-TB drug. Multidrug-resistant TB (MDR TB) is resistant to more than one anti-TB drug including e.g., at least isoniazid (INH) and rifampin (RIF). In some instances, confirmation of drug-resistant and multi-drug resistant TB is performed by drug-susceptibility testing. In some instances, TB assessments that include monitoring of TB treatment, e.g., using the TB assessments described herein, may be used to detect drug-resistant and multi-drug resistant TB before or concurrent with drug-susceptibility testing.

Compositions

The present disclosure provides compositions useful in practicing the methods disclosed herein for making TB assessments of subjects, such as diagnosing and clinically monitoring TB in a subject by detecting the levels of host TB biomarkers present on the surface of cells obtained from the subject. In some instances, compositions of the present disclosure include assessment compositions, including e.g., TB monitoring compositions and TB diagnosis compositions.

Such compositions may include one or more detection reagents that detect aforementioned host TB biomarkers, and in some instances, such detection reagents may be referred to herein as binding members or host TB biomarker binding members. Such binding members may contain a label domain that may be detected by a device, e.g., a flow cytometer, thus allowing qualitative identification or quantification of the level of the host TB biomarker present on a particular event detected by the device, e.g., a cell detected by a flow cytometer. In some instances, such binding members may contain a label binding domain such that the binding member may be detectably labeled by contacting a solution containing the binding member with a detectable label that binds the label binding domain, e.g., contacting a solution containing the binding member with a secondary antibody that is detectably labeled. Any detectably label may be used either in directly or indirectly detectably labeling a binding member of the instant disclosure including those known in the art and those described elsewhere herein.

In some instances, compositions of the instant disclosure may include two or more binding members. Such binding members included in compositions of two or more binding members may be detectably labeled such that each class of binding member, e.g., each binding member that binds a particular biomarker is particularly detectable, i.e. each biomarker detection event is recognizable as to the biomarker bound by a particular binding member. For example, in a composition that includes two binding members that detect two different biomarkers the binding members are detectably labeled with labels that are distinguishable by the detection device. In some instances, binding members included in compositions of two or more binding members may be detectably labeled such that two or more binding members share essentially the same detectable label, e.g., two or more binding members are detectably labeled with labels that cannot be distinguished by the detection device. Additional labeled binding members may also be provided. For example, the reagent device may include three, four or more distinct binding members. While the number of distinct labeled binding members may vary, in some instances the number ranges from two to twenty, such as three to fifteen, including four to ten. In addition, compositions may include one or more additional detectable labels that specifically bind additional cellular markers, e.g., cellular markers that identify an additional characteristic of a cell, e.g., a characteristic other than expression of a particular TB associated biomarker on the surface of the cell. Detectable labels may bind cellular markers directly or indirectly, i.e. through common binding of a labeled binding mediator. Examples of specific biomarkers for which a labeled binding member may be present in a given composition include, but are not limited to: CD154, CD45RA, CD197(CCR7), CD27, CD28, CD69, IFN-$\gamma$, IL-2, TNF-$\alpha$, Ki-67, HLA-D4, CD-38, CXCR3, CCR6, CD161, CD3, CD4 and/or CD8, e.g., as described above.

In some instances, compositions (such as described above) are configured as reagent devices. Reagent devices according to certain embodiments of the present disclosure include a solid support and a least first and second labeled binding members, e.g., as described above. The solid support included in the reagent devices of these embodiments can be any convenient solid support that is compatible with the liquid sample and/or reagent(s) or analyte(s) in contact with the reagent device. For example, the solid support can be a liquid-compatible solid support for reagent devices configured to contain a liquid sample. In some cases, the liquid sample may be an aqueous liquid sample, and in these cases, the solid support may be compatible with aqueous samples. By "compatible" is meant that the solid support is substantially inert (e.g., does not significantly react with) the liquid and/or reagent(s) or analyte(s) in contact with the solid support.

The solid support may be configured as a container, where the container is configured to hold a certain volume of a fluid (e.g., gas or liquid). In certain embodiments, the solid support is configured as a liquid container. For example, the liquid container may be configured to hold a volume of a liquid. The size of the liquid container may depend on the volume of liquid to be held in the liquid container. For instance, the liquid container may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the liquid container is configured to hold a volume (e.g., a volume of a liquid) ranging from 0.1 ml to 200 ml.

The shape of the solid support may also vary and may depend on the use of the reagent device. For example, as described herein, the reagent device may find use in an assay, such as an assay of a liquid sample (e.g., a biological sample). In these cases, the solid support may be configured in a shape that is compatible with the assay and/or the method or other devices used to perform the assay. For instance, the solid support may be configured in a shape of typical laboratory equipment used to perform the assay or in a shape that is compatible with other devices used to perform the assay. As described above, the solid support may be configured as a liquid container. In these embodiments, the liquid container may be a vial or a test tube. In certain cases, the liquid container is a vial. In certain cases, the liquid container is a test tube. As described above, the liquid container may be configured to hold a volume (e.g., a volume of a liquid). In embodiments where the liquid container is a vial or a test tube, the liquid container may be configured to hold a volume (e.g., a volume of a liquid) ranging from 0.1 ml to 1000 ml, such as from 0.5 ml to 900 ml, or 0.5 ml to 800 ml, or 0.5 ml to 700 ml, or 0.5 ml to 600 ml, or 0.5 ml to 500 ml, or 0.5 ml to 400 ml, or 0.5 ml to 300 ml, or 0.5 ml to 200 ml, or 0.5 ml to 100 ml, or 0.5 ml to 50 ml, or 0.5 ml to 25 ml, or 0.5 ml to 10 ml, or 0.5 ml to 5 ml, or 1 ml to 5 ml. In certain instances, the vial or test tube is configured to hold a volume (e.g., a volume of a liquid) ranging from 0.5 ml to 5 ml.

In other embodiments, the solid support is configured as a multi-well plate. In these cases, the solid support may include a plurality of liquid containers (e.g., wells), such as 2 or more, or 10 or more, or 50 or more, or 75 or more, or 100 or more, or 300 or more, or 500 or more, or 750 or more, or 1000 or more or 1500 or more, or 2000 or more liquid containers (e.g., wells). Examples of solid supports configured as multi-well plates may include, for example, 6, 24, 96, 384 or 1536 liquid containers (e.g., wells). In embodiments where the liquid container is a well of a multi-well plate, an individual well may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

As described above, embodiments of the solid support of the reagent device can be compatible with the liquid sample and/or reagent(s) or analyte(s) in contact with the reagent device. Examples of suitable solid support materials for the reagent devices include, but are not limited to, glass and plastic. For example, the solid support may be composed of glass, such as, but not limited to, silicate glass, borosilicate glass, sodium borosilicate glass (e.g., PYREX™), fused quartz glass, fused silica glass, and the like. Other examples of suitable solid support materials for the reagent devices include plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

In some embodiments, as described above, the solid support is configured as a container, where the container is configured to hold a certain volume of a fluid (e.g., gas or liquid, e.g., a liquid container). In some embodiments where the solid support is configured as a liquid container, the liquid container may be sealed. That is, the liquid container may include a seal that substantially prevents the contents of the liquid container (e.g., liquid inside the liquid container) from exiting the liquid container. The seal of the liquid container may also substantially prevent other substances from entering the liquid container. For example, the seal may be a water-tight seal that substantially prevents liquids from entering or exiting the container, or may be an air-tight seal that substantially prevents gases from entering or exiting the container. In some instances, the seal is a removable or breakable seal, such that the contents of the liquid container may be exposed to the surrounding environment when so desired, e.g., if it is desired to remove a portion of the contents of the liquid container. In some instances, the seal is made of a resilient material to provide a barrier (e.g., a water-tight and/or air-tight seal) for retaining a sample in the container. Particular types of seals include, but are not limited to, films, such as polymer films, caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the container. For instance, a threaded cap can be screwed over the opening before or after a sample has been added to the container.

As described above, the solid support may be configured as a container, where the container is configured to hold a certain volume of a fluid (e.g., gas or liquid). In some instances, a solid support that is configured as a container (e.g., a liquid container) has an inner surface and an outer surface. In these embodiments, the inner surface of the solid support (e.g., container) is the surface of the solid support (e.g., container) facing toward the inside of the solid support (e.g., container). The inner surface may be in contact with the contents of the container. As such, the solid support may include an inner surface of the container, such as an inner surface of a liquid container. The outer surface of the solid support (e.g., container) is the surface of the solid support (e.g., container) facing away from the inside of the solid support (e.g., container). The outer surface does not contact the contents of the container. As such, the solid support may include an outer surface of the container, such as an outer surface of a liquid container.

In certain embodiments, the labeled binding member compositions are dried compositions. A dried composition is a composition that includes a low amount of solvent. For example, dried compositions may include a low amount of a liquid, such as water. In some cases, a dried composition includes substantially no solvent. For instance, dried compositions may include substantially no liquid, such as water.

In certain embodiments, a dried composition includes 25 wt % or less solvent, such as 20 wt % or less, or 15 wt % or less, or 10 wt % or less, or 5 wt % or less, or 3 wt % or less, or 1 wt % or less, or 0.5 wt % or less solvent. In some cases, a dried dye composition is not a fluid. In some cases, a dried composition is substantially a solid. For example, a dried composition may have a high viscosity, such as a viscosity of 10,000 cP or more, or 25,000 cP or more, or 50,000 cP or more, or 75,000 cP or more, or 100,000 cP or more, or 150,000 cP or more, or 200,000 cP or more, or 250,000 cP or more at standard conditions.

In some instances, the compositions are lyophilized compositions. In certain cases, a lyophilized composition is a composition where water has been removed from the composition by sublimation, where the water in the composition undergoes a phase transition from a solid to a gas. For example, a lyophilized composition may be a composition where water has been removed from the composition by freezing the composition (e.g., freezing water in the dye composition) and then reducing the pressure surrounding the composition such that the water in the composition undergoes sublimation. In certain instances, a lyophilized composition includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In some cases, a lyophilized composition has 3% or less water as measured by Karl Fischer titration. In some cases, a lyophilized composition has 1% or less water as measured by Karl Fischer titration. In some cases, a lyophilized composition has 0.5% or less water as measured by Karl Fischer titration. Lyophilized compositions may include additives and/or excipients, such as a stabilizer. In some cases, the lyophilized composition includes a stabilizer, such as a sugar or a polyalcohol. Sugars and polyalcohols suitable for use in lyophilized compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof.

Devices and Systems

Aspects of the invention further include systems for use in practicing the subject methods. Systems of the invention may include a flow cytometry system configured to assay cellular samples (e.g., whole blood, PBMCs, etc.) by measuring signals such as FSC, SSC, ALL, fluorescence emission (e.g., as emission maxima), mass, molecular mass, etc. Steps of the methods described in the previous sections may be performed by the flow cytometry system.

In some instances, the flow cytometer includes: a flow channel; a detector module that includes a first detector configured to receive a first signal from the assay region of the flow channel and a second detector configured to receive a second signal from the assay region of the flow channel. The flow cytometer may optionally further include at least a first light source configured to direct light to an assay region of the flow channel (where in some instances the cytometer includes two or more light sources). Optionally further, the flow cytometer may include one or more additional detectors and/or light sources for the detection of one or more additional signals. The one or more additional signals may be produced by one or more additional detectable labels.

The flow cytometer may be configured to produce a data set. The data set may include signal data (e.g., fluorescence excitation and/or emission spectra, fluorescence intensity, fluorescence emission maxima, FSC, SSC, ALL or combinations thereof) for each event in the data set.

The flow cytometry system may also include a "data processing unit", e.g., any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

The flow cytometry system may further include a "memory" that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

The memory may store a "module" for execution by the data processing unit, wherein the module is configured to transform the data set from a number transform the data set from a number (X) of signal sets to a number (Y) of marker density sets, wherein Y>X. The marker density sets may include marker expression data (e.g., levels and/or amounts of cellular markers, signals from detectible labels corresponding to cellular markers, etc.) for each cell event in the data set or in a population thereof. The module may be configured to transform the data set based on a categorization of events (e.g. cell events) in the signal set. For example, the same fluorescent signal obtained from two cell events categorized into separate populations may be provided by different detectable labels specific for different cell marker. The module may be configured to distinguish detectable labels (e.g., detectable labels providing a substantially identical signal) based on the categorization.

In certain aspects, the module may be configured to categorize the cell events prior to transforming the data set. Further, the module may be configured to categorize the cell events based on measurements of FSC, SSC, ALL, fluorescence emission or combinations thereof. In other aspects, the cell events may be categorized by an operator (i.e., manually) as described previously.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

Suitable flow cytometry systems and methods for analyzing samples include, but are not limited to those described in Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); Practical Flow Cytometry, 3rd ed., Wiley-Liss (1995); Virgo, et al. (2012) Ann Clin Biochem. January; 49(pt 1):17-28; Linden, et. al., Semin Throm Hemost. 2004 October; 30(5):502-11; Alison, et al. J Pathol, 2010 December; 222(4):335-344; and Herbig, et al. (2007) Crit Rev Ther Drug Carrier Syst. 24(3):203-255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSR-Fortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, BD FACSLyric™ flow cytometer, or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

In some instances, the systems may further include a cellular sample (e.g., loaded on the flow channel), as prepared according to any of the aspects of the subject methods described above. In certain aspects, the flow cytometer may be a fluorescence activated cell sorter (FACS) instrument or an automated or semi-automated flow cytometer optionally including semi-automated custom flow cytometry software and/or semi- or fully automated liquid handling for staining, semi- or automated flow cytometry for data acquisition, and standardized algorithms for automated data analysis. In certain instances, the device may be a high through put system or include a high through put component.

Utility

The present disclosure provides methods for the identification of subpopulations of cells collected from subjects suspected of having TB, subjects known to have TB, and patients being treated for TB and the like. Such methods have a number of useful applications described below.

As reviewed above, TB assessments obtained in accordance with embodiments of the invention find use in both diagnostic and treatment monitoring applications. For example, TB assessments find use in diagnostic applications, such as diagnosing the presence of TB, diagnosing the type of TB, e.g., LTBI, ATB, etc., diagnosing a transition for LTBI to ATB, etc.

Aspects of the methods described herein include identification of subpopulations of cells expressing TB biomarkers above or below a particular threshold level useful in obtaining a TB biomarker signature that can be used in monitoring progression of TB in a subject, e.g., by detecting a first biomarker signature of a blood sample obtained from a subject at a first time point and detecting a second biomarker signature of a blood sample at a second time point and comparing the first and second biomarker signatures to make an assessment of TB progression, wherein the assessment provides for monitoring of the progression of TB from the first time point to the second time point. TB progression may be monitored in TB patients undergoing treatment or patients not undergoing TB, e.g., those patients known to be infected with TB, e.g., those having latent TB, but not undergoing treatment. In certain instances, more than two time points may be utilized in monitoring TB progression.

In certain embodiments, the method of monitoring progression of TB in a subject allows for detecting a pattern of biomarker signatures present in a plurality of samples, e.g., blood samples, obtained from a subject at more than two time points, such as three or more, four or more, five or more, six or more, seven or more, eight or more, nine or more, or ten or more. In general, the time points for detecting a pattern of biomarker signatures can be separated by any amount of time that is desired. For example, the first time point and second time point can be separated by less than 1 week, about 1 week, about 2 weeks, about 3 weeks, about 4 weeks, about 5 weeks, about 6 weeks, about 1 month, about 2 months, about 3 months, about 6 months, or about 1 year or more, such as about 3 or more years.

In general, it will be appreciated by one of skill in the art that the duration of time between the first time point and the second time point must be sufficient to provide for a monitoring of the progression of the TB disease, e.g., the monitoring of TB during TB treatment.

In certain embodiments, the methods of monitoring TB presented herein allow for parallel monitoring of disease progression and disease treatment, e.g., during a treatment regimen for TB. In such embodiments, the method of monitoring TB during treatment will provide information of whether the treatment is improving the condition, or having no effect or an adverse effect on the condition. In such embodiments, the first time point may be either just before, concurrent with, or just after the initiation of a treatment regimen and the second time point may be a time point following a desired treatment period. For example, in such embodiments, the second time point may be about 1 week or more following initiation of treatment, including about 2 weeks, about 3 weeks, about 4 weeks, about 5 weeks, about 6 weeks, about 1 year, about 2 years, or more. For example, the detection of the biomarker signature present in a blood sample obtained from the subject may be determined about once every week or more, including once every two weeks, once every three weeks, once every four weeks, once every five weeks, once every six weeks, once every 2 months, once every 3 months, once every 4 months, once every 5 months, once every 6 months, once every year, once every 2 years, and once every 3 years, to monitor TB progression and efficacy of the treatment regimen.

Certain aspects of the methods, devices, systems and kits presented herein provide for greater efficacy of treatment monitoring and thus great efficacy of treatment as treatments may be tailored to a particular patient's response to treatment. For example, in some instances treatment may be continued longer than intended at the onset of treatment based on a TB assessment performed during treatment that indicates that longer treatment is necessary. In other instances treatment may be discontinued earlier than intended at the onset of treatment based on a TB assessment performed during treatment that indicates that the initially prescribed treatment length is unnecessary.

In certain aspects of the present disclosure, TB assessments are made by comparison of biomarker evaluations or measurements or biomarker signatures to a reference standard. In certain embodiments, methods described herein are useful in deriving such reference standards. In some instances, the reference standard with which a particular subject or patient sample is compared, as described herein, is the patient's or subject's own sample, e.g., the patient's or subject's own sample collected at an earlier time point. In some embodiments, TB monitoring may be performed by making TB assessments, as described herein, by comparison of samples, e.g., patient blood samples or cells of a patient, acquired at different times and/or under different conditions, e.g., at different times during a treatment regimen or under different treatment conditions, e.g., under different treatment regimens or during different phases of treatment.

Reagents and Kits

Also provided are reagents, devices and kits thereof for practicing one or more of the above-described methods. The subject reagents, devices and kits thereof may vary greatly. Reagents and devices of interest include those mentioned above with respect to the methods of detection of biomarkers and identification of subpopulations of cells expressing biomarkers, e.g., by flow cytometry. The subject kits may include a first detectable label that specifically binds to a first cellular marker and a second detectable label that specifically binds to a second biomarker. The first and second detectable labels may provide a substantially identical signal or substantially different signals. A detectable label may include a label domain and a binding member specific for a biomarker, as described in the previous section. As reviewed above, specific biomarkers of interest for which a given kit may include a detectible binding member include, but are not limited to: CD154, CD45RA, CD197(CCR7), CD27, CD28, CD69, IFN-γ, IL-2, TNF-α, Ki-67, HLA-D4, CD-38, CXCR3, CCR6, CD161, CD3, CD4 and/or CD8, e.g., as described above.

Kits useful for practicing one or more of the above-described methods may include one or more of such reagents and devices including e.g., reagents and devices for biomarker detection, reagents and devices for identification of subpopulations of cells expressing one or more biomarkers, reagents and devices for collecting, storing, preparing, processing, samples prior or during execution of any of the methods described herein, and devices for interpreting, storing, converting, displaying, or disseminating data pertaining to assessments made according to the methods described herein. In addition, the kits may include one or more calibration or reference reagents, e.g., for use in calibration of a device, including e.g., a flow cytometer, or for configuration of a device, including e.g., configuration of a flow cytometer, including e.g., configuration of threshold values, e.g., biomarker threshold values, to be used in assessments as described herein. In addition, the kit may include one or more additional compositions that are employed, including but not limited to: buffers, diluents, cell lysing agents, etc., which may be employed in a given assay. The above components may be present in separate containers or one or more components may be combined into a single container, e.g., a glass or plastic vial.

In addition, the kit may include one or more additional detectable labels that specifically bind additional cellular markers, e.g., cellular markers that identify an additional characteristic of a cell, e.g., a characteristic other than expression of a particular TB biomarker on the surface of the cell. Detectable labels may bind cellular markers directly or indirectly, i.e. through common binding of a label binding mediator. Detectable labels may be provided in separate containers or mixed in the same container.

The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The kit may further include reagents for performing a flow cytometric assay. Examples of said reagents include buffers for at least one of reconstitution and dilution of the first and second detectable molecules, buffers for contacting a cell sample with one or both of the first and second detectable molecules, wash buffers, control cells, control beads, fluorescent beads for flow cytometer calibration and combinations thereof.

The detectable labels and/or reagents described above may be provided in liquid or dry (e.g., lyophilized) form. Any of the above components (detectable labels and/or reagents) may be present in separate containers (e.g., separate tubes, bottles, or wells in a multi-well strip or plate). In addition, one or more components may be combined into a single container, e.g., a glass or plastic vial, tube or bottle.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, removable drive, flash drive, etc., on which the information has been recorded. Yet another means that may be present is a website address which may be used via the internet to access the information at a removed site. Any convenient means may be present in the kits.

The following examples are offered by way of illustration and not by way of limitation.

EXAMPLES

I. Protocol

Whole blood samples are activated in vitro with Unit dose of dried stimulating reagent containing TB-specific 15mer peptide pool mixes representing MTB proteins (e.g. ESAT-6, CFP) or a positive control stimulus. Activation occurs in the presence of CD28+CD49d costimulatory antibodies and a secretion inhibitor (e.g., Brefeldin-A (BFA), Monensin), along with fluorescent dye-conjugated CD154. Activation time: 6-24 hours at 37° C. After activation, the activated blood sample is treated with EDTA (10 mM) for 15 min at room temperature. Red blood cells are then lysed with Lysing reagent, followed by washing the cells with PBS/BSA/azide (wash buffer). The resultant sample is stained with a unit does of a fluorescent conjugated antibody panel CD3, CD4 and CD8, and T-cell central memory differentiation markers (CD45RA, CCR7, CD27, CD28) defining memory cell subsets (Central memory subsets and Effector Memory subsets). The stained samples are analyzed using a flow cytometer (e.g., FACSLyric). Flow cytometry data analysis is performed using an analysis algorithm to calculate the net frequency (i.e., response) of TB-specific activated T cells after subtracting the response of unstimulated control sample.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of assaying a Tuberculosis (TB) antigen activated sample consisting essentially of:
   producing a Tuberculosis (TB) activated sample from a subject;
   contacting the TB antigen activated sample with labeled specific binding members that specifically bind to CD154, CD45RA, CD197(CCR7), CD27, and CD28 to determine a T cell phenotype; and
   detecting the presence of:
   (i) $CD154^+$ T cells; and
   (ii) T cells having a central memory 1 (CM1) phenotype ($CD45RA^-$, $CD197(CCR7)^+$, $CD27^+$, $CD28^+$), central memory 2 (CM2) phenotype ($CD45RA^-$, $CD197(CCR7)^{+/-}$, $CD27^+$, $CD28^+$) or a central memory 3 (CM3) phenotype ($CD45RA^-$, $CD197(CCR7)^-$, $CD27^+$, $CD28^+$); thereby determining the T cell phenotype of
   the TB antigen activated sample from the subject.

2. The method according to claim 1, wherein the method does not include assaying the sample for any intracellular markers.

3. The method according to claim 1, wherein the sample is a blood sample.

4. The method according to claim 3, wherein the blood sample is a whole blood sample.

5. The method according to claim 1, wherein producing the TB antigen activated sample comprises:
   obtaining a cellular sample from the subject; and
   contacting the cellular sample with a *Mycobacterium tuberculosis* (MTB) antigen.

6. The method according to claim 5, wherein the method further comprises contacting the sample with a co-stimulatory reagent.

7. The method according to claim 6, wherein the co-stimulatory reagent comprises CD28 and CD49d specific binding members.

8. The method according to claim 1, wherein the detecting comprises flow cytometrically analyzing the TB antigen activated sample.

9. The method according to claim 1, wherein the method further comprises quantitating the number or proportion of CD154+ T cells and T cells having a CM1 phenotype ($CD45RA^-$, $CD197(CCR7)^+$, $CD27^+$, $CD28^+$), CM2 phenotype ($CD45RA^-$, $CD197(CCR7)^{+/-}$, $CD27^+$, $CD28^+$) or a CM3 phenotype ($CD45RA^-$, $CD197 (CCR7)^-$, $CD27^+$, $CD28^+$) in the TB antigen activated sample from the subject.

10. The method according to claim 9, wherein the method further comprises identifying a TB treatment regimen based on the number or proportion of CD154+ T cells and T cells having a CM1 phenotype, CM2 phenotype, or CM3 phenotype.

11. The method according to claim 10, wherein the method further comprises administering the TB treatment regimen to the subject.

12. The method according to claim 9, wherein the number or proportion of CD154+ T cells and T cells having a CM1 phenotype, CM2 phenotype, or CM3 phenotype indicates the subject has a latent tuberculosis infection (LTBI) or active tuberculosis (ATB).

13. The method according to claim 9, wherein the number or proportion of CD154+ T cells and T cells having a CM1 phenotype, CM2 phenotype, or CM3 phenotype indicates a transition between LTBI and ATB.

14. The method according to claim 1, wherein the method further comprises contacting the TB antigen activated sample with labeled specific binding members for one or more of CD57, CD69, IFN-γ, IL-2, TNF-α, Ki-67, HLA-D4, CD-38, CXCR3, CCR6, CD161, CD3, CD4, and CD8.

15. The method according to claim 1, wherein the method further comprises quantitating the level of CD45RA, CD197 (CCR7), CD27 and CD28 expressed by cells in the TB antigen activated sample to identify the number or proportion of T cells having a CM1 phenotype, CM2 phenotype, or CM3 phenotype.

* * * * *